US011602746B2

(12) United States Patent
Kim et al.

(10) Patent No.: US 11,602,746 B2
(45) Date of Patent: Mar. 14, 2023

(54) CHEMICALLY PATTERNED MICROFLUIDIC PAPER-BASED ANALYTICAL DEVICE (C-μPAD) FOR MULTIPLEX ANALYTE DETECTION

(71) Applicant: Texas Tech University System, Lubbock, TX (US)

(72) Inventors: Jungkyu Kim, Lubbock, TX (US); Jasmine Pramila Devadhasan, Lubbock, TX (US); Ryan Howse, El Paso, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 657 days.

(21) Appl. No.: 16/102,294

(22) Filed: Aug. 13, 2018

(65) Prior Publication Data

US 2019/0118175 A1    Apr. 25, 2019

Related U.S. Application Data

(63) Continuation-in-part of application No. 15/135,326, filed on Apr. 21, 2016, now abandoned.

(60) Provisional application No. 62/150,387, filed on Apr. 21, 2015.

(51) Int. Cl.
| | |
|---|---|
| *B01L 3/00* | (2006.01) |
| *G01N 21/78* | (2006.01) |
| *C12Q 1/54* | (2006.01) |
| *G01N 33/68* | (2006.01) |
| *G01N 33/18* | (2006.01) |
| *G01N 33/52* | (2006.01) |

(52) U.S. Cl.
CPC ...... *B01L 3/502707* (2013.01); *B01L 3/502715* (2013.01); *C12Q 1/54* (2013.01); *G01N 21/78* (2013.01); *G01N 33/1813* (2013.01); *G01N 33/52* (2013.01); *G01N 33/6863* (2013.01); *B01L 2300/0816* (2013.01); *B01L 2300/126* (2013.01); *B01L 2300/161* (2013.01); *G01N 2333/525* (2013.01)

(58) Field of Classification Search
CPC ................................................ B01L 3/502707
USPC ....................................................... 422/504
See application file for complete search history.

(56) References Cited

PUBLICATIONS

Chen et al. "Patterned Fluoropolymer Barriers for Containment of Organic Solvents within Paper-Based Microfluidic Devices" ACS Appl. Mater. Interfaces 2013, 5, 12701-12707. (Year: 2013).*

(Continued)

*Primary Examiner* — Christine T Mui
*Assistant Examiner* — Emily R. Berkeley
(74) *Attorney, Agent, or Firm* — Dickinson Wright PLLC; Kristopher Lance Anderson

(57) ABSTRACT

Disclosed is a device and method for a microfluidic paper-based analytical device (μPAD), for low-cost and user-friendly analytical devices capable of use for disease screening, point-of-care pathogen and biomarker detection, food and water quality testing. A microfluidic paper-based analytical device is further produced by chemical vapor deposition for multiplex heavy metal detection in water. Assay demonstrations proved that the immobilization of functional groups and multiplex heavy metal detection is suitable for real-world applications and established the approach for DNA analysis. The disclosed invention comprises multilayer capability, including the ability for various biomolecules to be immobilized with charge interaction.

18 Claims, 15 Drawing Sheets

(56) References Cited

PUBLICATIONS

Missoum et al. "Nanofibrillated Cellulose Surface Modification: A Review" Materials 2013, 6, 1745-1766 (Year: 2013).*
M. Li, R. Cao, A. Nilghaz, L. Guan, X. Zhang, W. Shen, "Periodic-Table-Style" paper device for monitoring heavy metals in water, Anal. Chem. 87 (2015) 2555-2559.
R.S. Boyd, Heavy metal pollutants and chemical ecology: exploring new frontiers, J. Chem. Ecol. 36 (2010) 46-58.
N. Johri, G. Jacquillet, R. Unwin, Heavy metal poisoning: the effects of cadmium on the kidney, Biometals 23 (2010) 783-792.
S.M.Z. Hossain, J.D. Brennan, β-Galactosidase-based colorimetric paper sensor for determination of heavy metals, Anal. Chem. 83 (2011) 8772-8778.
V.A. Lemos, A.L. de Carvalho, Determination of cadmium and lead in human biological samples by spectrometric techniques: a review, Env. Monitor. Assess. 171 (2010) 255-265.
D.J. Butcher, Advances in Inductively Coupled Plasma Optical Emission Spectrometry for Environmental Analysis, Instrum. Sci. Technol. 38 (2010) 458-469.
J. Feldmann, P. Salaün, E. Lombi, Critical review perspective: elemental speciation analysis methods in environmental chemistry moving towards methodological integration, Environ. Chem. 6 (2009) 275-289.
M. Li, H. Gou, I. Al-Ogaidi, N. Wu, Nanostructured sensors for detection of heavy metals: a review, ACS Sustainable Chem. Eng. 1 (2013) 713-723.
Y. Lin, D. Gritsenko, S. Feng, Y.C. Teh, X. Lu, J. Xu, Detection of heavy metal by paper-based microfluidics, Biosens. Bioelectron. 83 (2016) 256-266.
Y. Tian, Y. Wang, Y. Xu, Y. Liu, D. Li, C. Fan, A highly sensitive chemiluminescence sensor for detecting mercury (II) ions: a combination of Exonuclease III-aided signal amplification and graphene oxide-assisted background reduction, Sci. China Chem. 58 (2015) 514-518.
N.S. Kou, W. Shumi, M.H. Lee, S.W. Bae, J. Du, J.S. Kim, J.I Hong, X. Peng, J. Yoon, S. Park, Microfluidic detection of multiple heavy metal ions using fluorescent chemosensors, Bull. Korean Chem. Soc. 30 (2009) 1173-1176.
T. Krawczyński vel Krawczyk, M. Moszczyńska, M. Trojanowicz, Inhibitive determination of mercury and other metal ions by potentiometric urea biosensor, Biosens. Bioelectron. 15 (2000) 681-691.
X. Li, J. Tian, T. Nguyen, W. Shen, Paper-based microfluidic devices by plasma treatment, Anal. Chem. 80 (2008) 9131-9134.
K. Abe, K. Suzuki, D. Citterio, Inkjet-printed microfluidic multianalyte chemical sensing paper, Anal. Chem. 80 (2008) 6928-6934.
A.W. Martinez, S.T. Phillips, M.J. Butte, G.M. Whitesides, Patterned paper as a platform for inexpensive, low-volume, portable bioassays, Angew. Chem. Int. Ed. Engl. 46 (2007) 13181320.
D.A. Bruzewicz, M. Reches, G.M. Whitesides, Low-cost printing of poly(dimethylsiloxane) barriers to define microchannels in paper, Anal. Chem. 80 (2008) 3387-3392.
S. Su, M.M. Ali, C.D.M. Filipe, Y. Li, R. Pelton, Microgel-based inks for paper-supported biosensing applications, Biomacromolecules 9 (2008) 935-941.
A.W. Martinez, S.T. Phillips, G.M. Whitesides, Three-dimensional microfluidic devices fabricated in layered paper and tape, Proc. Natl. Acad. Sci. U.S.A. 105 (2008) 19606-19611.
J. Liu, H. Wang, N.E. Manicke, J.M. Lin, R.G. Cooks, Z. Ouyang, Development, characterization, and application of paper spray ionization, Anal. Chem. 82 (2010) 2463-2471.
A. Apilux, W. Dungchai, W. Siangproh, N. Praphairaksit, C.S. Henry, O. Chailapakul, Labon-Paper with dual electrochemical/colorimetric detection for simultaneous determination of gold and iron, Anal. Chem. 82 (2010) 1727-1732.
H. Noh, S.T. Phillips, Metering the Capillary-driven flow of fluids in paper-based microfluidic devices, Anal. Chem. 82 (2010) 4181-4187.
M.S. Khan, G. Thouas, W. Shen, G. Whyte, G. Garnier, Paper diagnostic for instantaneous blood typing, Anal. Chem. 82 (2010) 4158-4164.
A.W. Martinez, S.T. Phillips, E. Carrilho, S.W. Thomas, H. Sindi, G.M. Whitesides, Simple telemedicine for developing regions: camera phones and paper-based microfluidic devices for real-time, off-site diagnosis, Anal. Chem. 80 (2008) 3699-3707.
R. Pelton, Bioactive paper provides a low-cost platform for diagnostics, Trends Anal. Chem. 28 (2009) 925-942.
X. Li, J. Tian, W. Shen, Thread as a versatile material for low-cost microfluidic diagnostics, Appl. Mater. Interfaces 2 (2010) 1-6.
Y. Lu, W. Shi, J. Qin, B. Lin, Fabrication and characterization of paper-based microfluidics prepared in nitrocellulose membrane by wax printing, Anal. Chem. 82 (2010) 329-335.
W. Zhao, M.M. Ali, S.D. Aguirre, M.A. Brook, Y. Li, Paper-based bioassays using gold nanoparticle colorimetric probes, Anal. Chem. 80 (2008) 8431-8437.
A.W. Martinez, S.T. Phillips, G.M. Whitesides, E. Carrilho, Diagnostics for the developing world: microfluidic paper-based analytical devices, Anal. Chem. 82 (2010) 3-10.
R.E. Luckham, J.D. Brennan, Bioactive paper dipstick sensors for acetylcholinesterase inhibitors based on sol-gel/enzyme/gold nanoparticle composites, Analyst 135(2010) 2028-2035.
E. Evans, E.F.M. Gabriel, W.K.T. Coltro, C.D. Garcia, Rational selection of substrates to improve color intensity and uniformity on microfluidic paper-based analytical devices, Analyst 139 (2014) 2127-2132.
D.L. Giokas, G.Z. Tsogas, A.G. Vlessidis, Programming fluid transport in paper-based microfluidic devices using razor-crafted open channels, Anal. Chem. 86 (2014) 6202-6207.
E. Evans, E.F.M. Gabriel, T.E. Benavidez, W.K.T. Coltro, C.D. Garcia, Modification of microfluidic paper-based devices with silica nanoparticles, Analyst 139 (2014) 5560-5567.
P. de Tarso Garcia, T.M. Garcia Cardoso, C.D. Garcia, E. Carrilho, W.K. Tomazelli Coltro, A handheld stamping process to fabricate microfluidic paper-based analytical devices with chemically modified surface for clinical assays, RSC Adv. 4 (2014) 37637-37644.
M.M. Mentele, J. Cunningham, K. Koehler, J. Volckens, C.S. Henry, Microfluidic paper based analytical device for particulate metals, Anal. Chem. 84 (2012) 4474-4480.
T. Lam, J.P. Devadhasan, R. Howse, J. Kim, A Chemically patterned microfluidic paperbased analytical device (C-µPAD) for point-of-care diagnostics, Sci. Rep. 7 (2017) 1188.
M. Abdelmouleh, S. Boufi, M.N. Belgacem, A. Dufresne, Short natural-fibre reinforced polyethylene and natural rubber composites: Effect of silane coupling agents and fibres loading, Compos. Sci. Technol. 67 (2007) 1627-1639.
H. Koga, T. Kitaoka, A. Isogai, In situ modification of cellulose paper with amino groups for catalytic applications, J. Mater. Chem. 21 (2011) 9356-9361.
M.E. Vlachopoulou, A. Tserepi, P. Pavli, P. Argitis, M. Sanopoulou, K. Misiakos, A low temperature surface modification assisted method for bonding plastic substrates, J. Micromech. Microeng. 19 (2009) 015007.
P.K. Jal, S. Patel, B.K. Mishra, Chemical modification of silica surface by immobilization of functional groups for extractive concentration of metal ions, Talanta 62 (2004) 1005-1028.
H. Lee, J. Yi, Removal of copper ions using functionalized mesoporous silica in aqueous solution, Sep. Sci. Technol. 36 (2001) 2433-2448.
P.B. Tchounwou, C.G. Yedjou, A.K. Patlolla, D.J. Sutton, Heavy metals toxicity and the environment, EXS 101 (2012) 133-164.
D. Oakley, N.E. Korte, Nickel and chromium in ground water samples as influenced by well construction and sampling methods, Ground Water Monit. Remediat. 16 (1996) 93-99.
B.F. Ye, Y.J. Zhao, Y. Cheng, T.T. Li, Z.Y. Xie, X.W. Zhao, et al., Colorimetric photonic hydrogel aptasensor for the screening of heavy metal ions, Nanoscale 4 (2012) 5998-6003.
E.L. Rossini, M.I. Milani, E. Carrilho, L. Pezza, H.R. Pezza, Simultaneous determination of renal function biomarkers in urine using a validated paper-based microfluidic analytical device, Anal. Chim. Acta 997 (2018) 16-23.

* cited by examiner

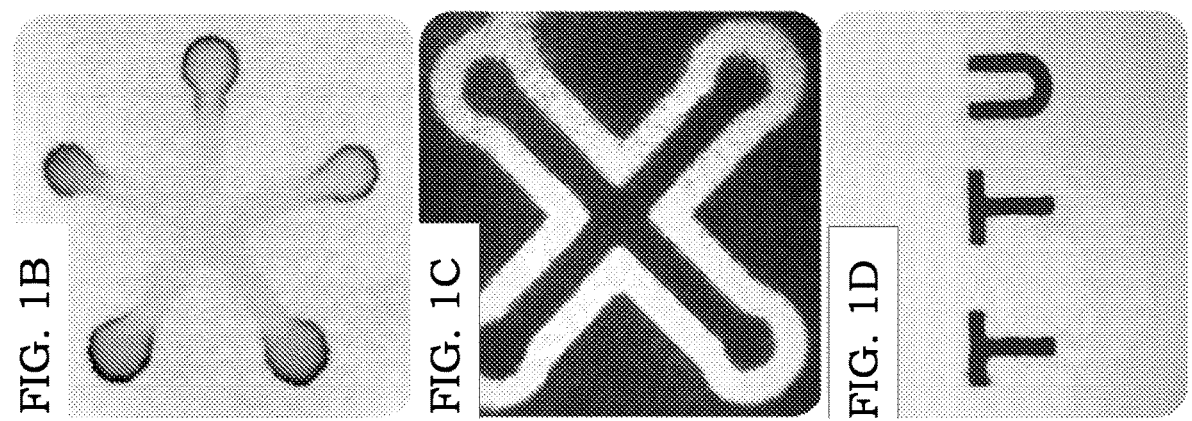
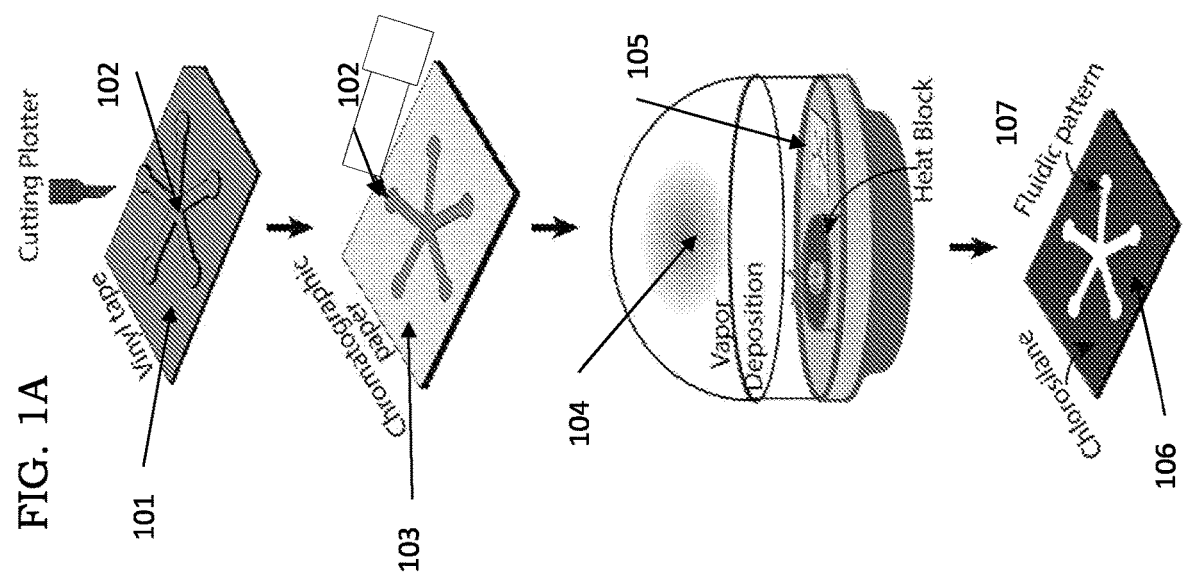

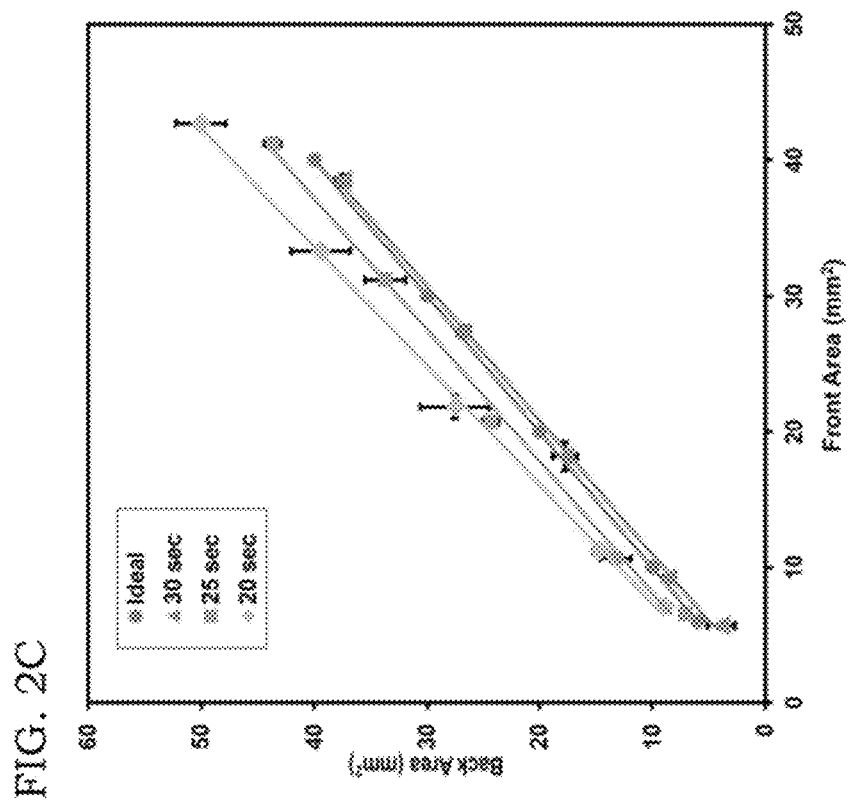
FIG. 2A
FIG. 2B
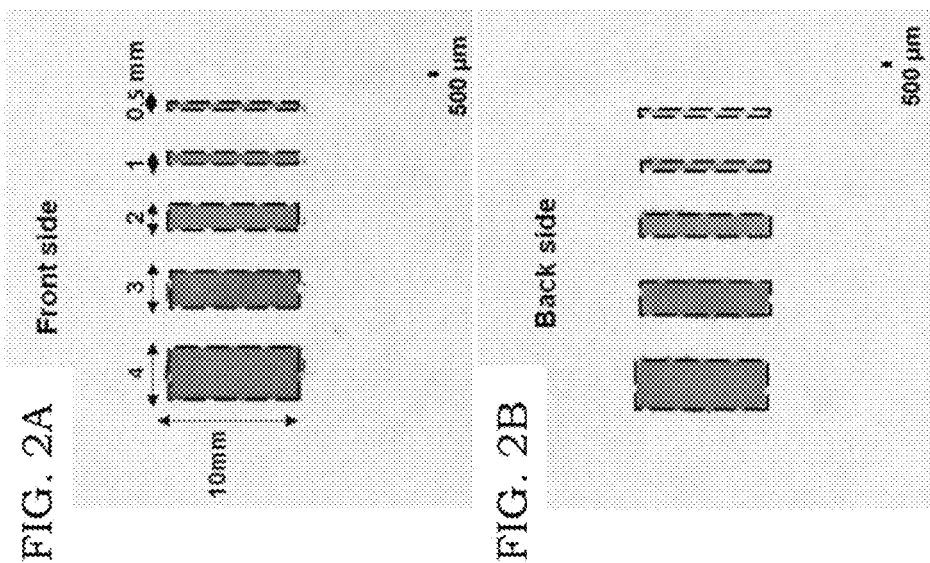
FIG. 2C

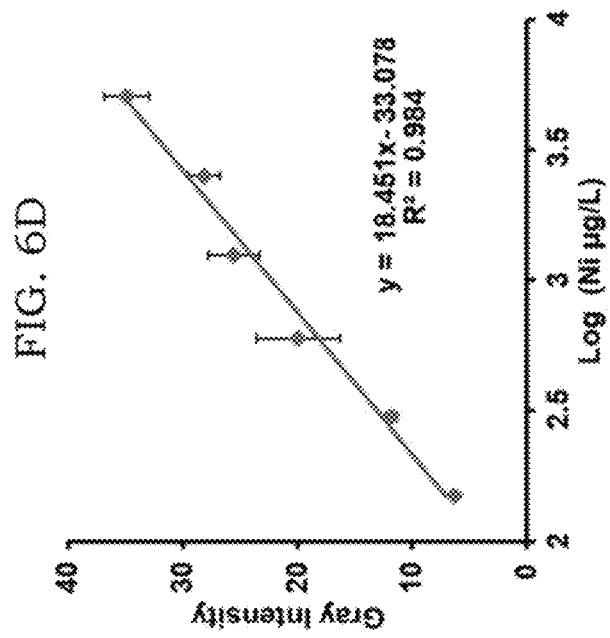
FIG. 6D
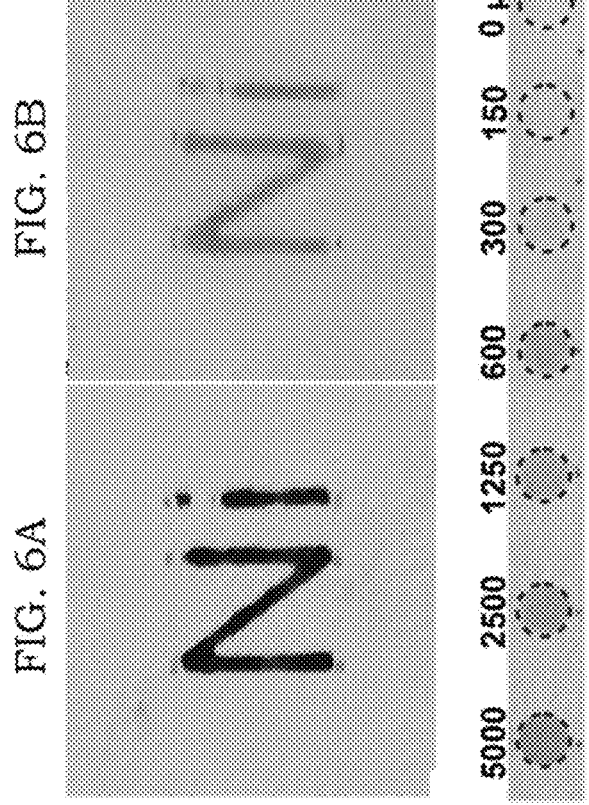
FIG. 6A  FIG. 6B
FIG. 6C

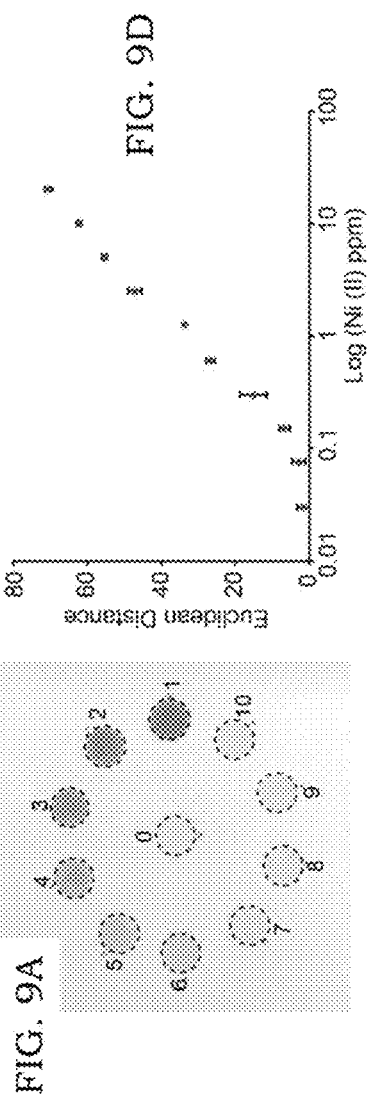

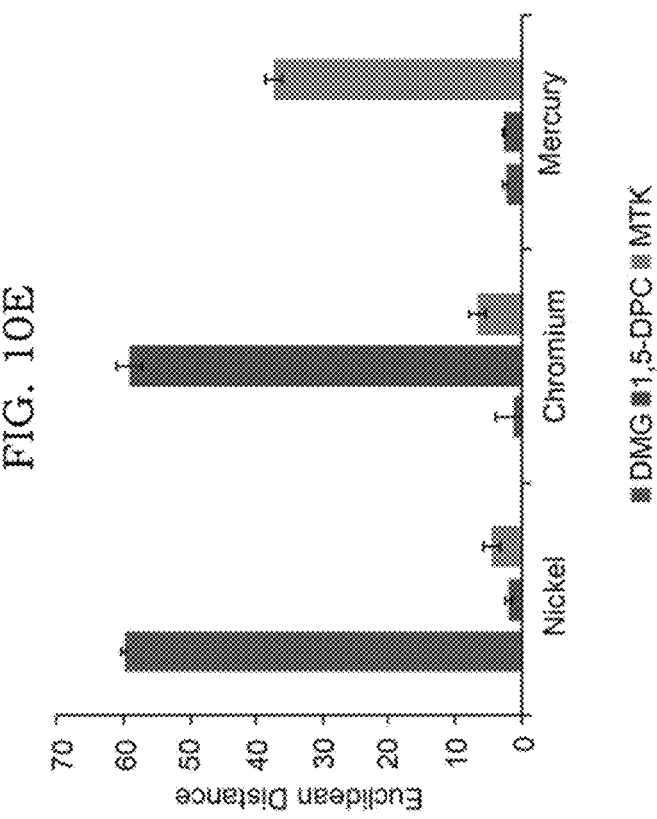
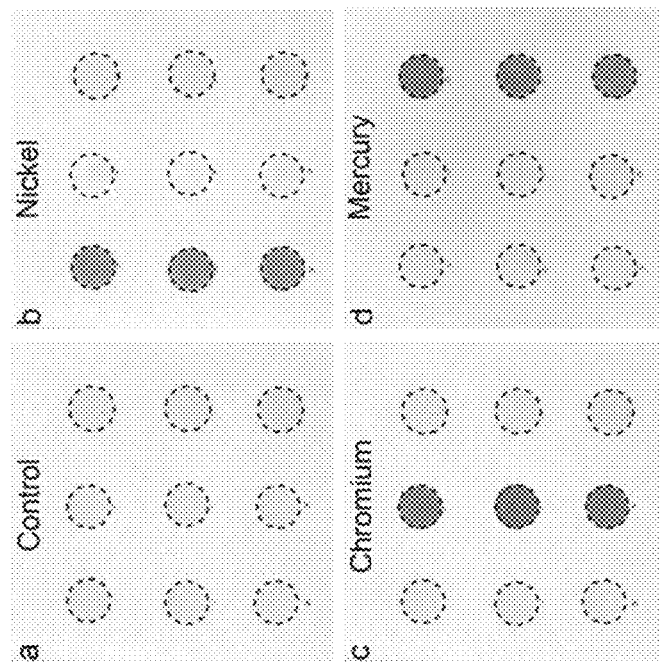

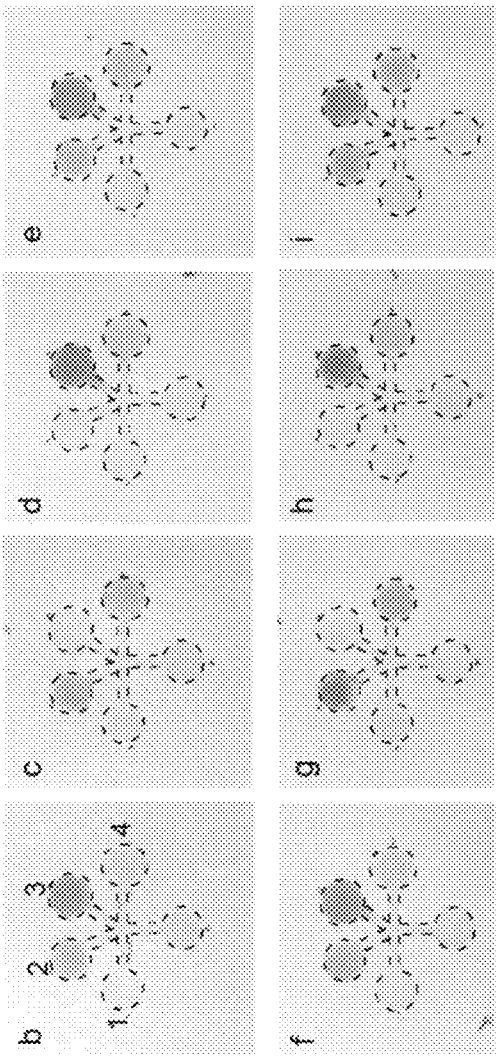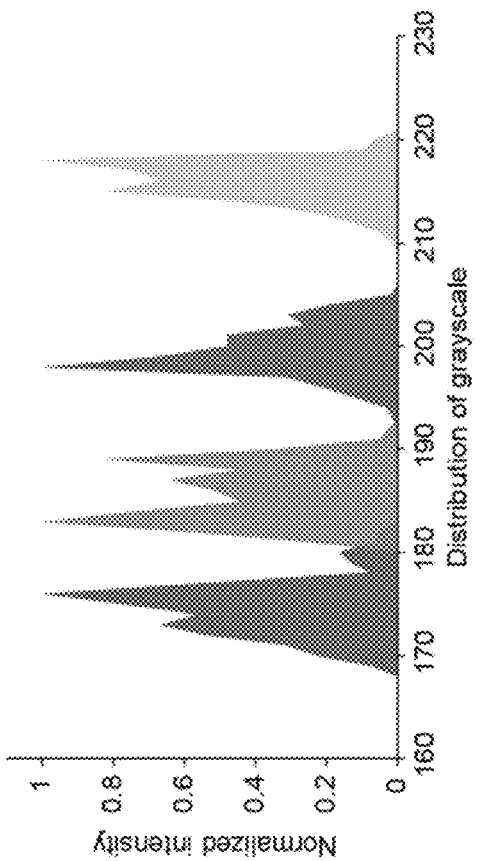

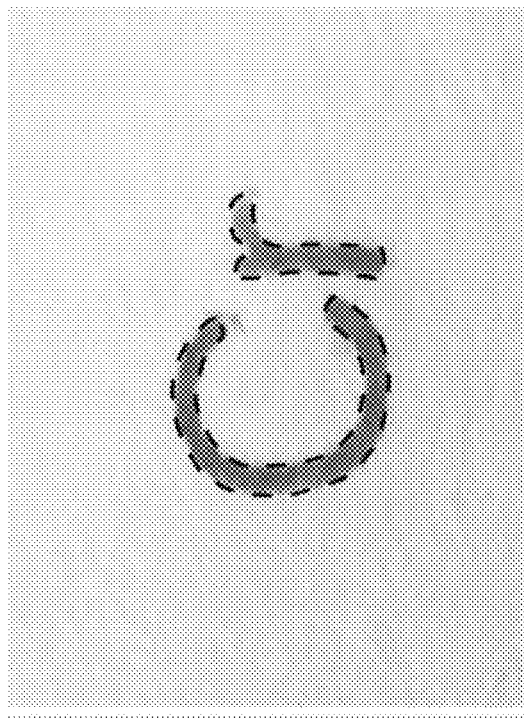
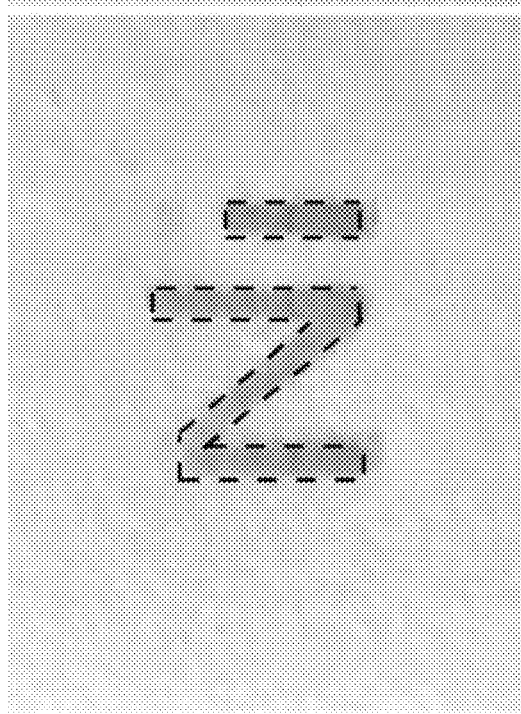
FIG. 12A
FIG. 12B

CHEMICALLY PATTERNED MICROFLUIDIC PAPER-BASED ANALYTICAL DEVICE (C-µPAD) FOR MULTIPLEX ANALYTE DETECTION

INCORPORATION BY REFERENCE TO APPLICATION

This application is a continuation-in-part of U.S. patent application Ser. No. 15/135,326, filed Apr. 21, 2016 entitled "System And Method For Chemically Patterned Paper Microfluidic Devices", which claims priority to U.S. Provisional Application Ser. No. 62/150,387 filed Apr. 21, 2015 entitled "System And Method For Chemically Patterned Paper Microfluidic Devices". This application is also related to U.S. Provisional Application Ser. No. 62/663,174, filed Apr. 26, 2018 entitled "Chemically Patterned Microfluidic Paper-Based Analytical Device (C-µPAD) For Multiplex Analyte Detection".

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of microfluidic devices. In particular, the system of the present invention provides for a microfluidic devices comprised of chemically patterned paper. The disclosed systems and methods support a wide variety of scenarios for diagnostic research and related products and services.

STATEMENT OF FEDERALLY FUNDED RESEARCH

None.

BACKGROUND OF THE DISCLOSURE

The microfluidic paper-based analytical device (µPAD) presents a promising alternative to traditional laboratory tests by allowing for the rapid and low-cost diagnoses of diseases in resource-limited settings. Recently, µPADs have received considerable attention since the world health organization (WHO) suggested that µPADs are promising diagnostic tools for the developing world. µPADs offer many advantages as simple and portable platforms that require only a drop of target sample for detecting various analytes such as proteins, environmental contaminants, pathogens, chemicals, heavy metals, and drugs. Unlike the active microfluidic devices, µPADs can transport target samples and reagents via capillary action without the need for mechanical components, external pumps, or controllers.

µPADs are fabricated by forming hydrophobic barriers onto various paper platforms. Currently, several techniques have been reported to fabricate µPADs such as photolithography, plotting with an analogue plotter, ink jet etching, plasma treatment, paper cutting, wax printing, inkjet printing, flexography printing, screen printing, and laser patterning techniques. The fundamental principle of these µPAD fabrication techniques is to form hydrophilic-hydrophobic barriers on a chromatography or filter paper to create fluidic channel networks. Liquid follows hydrophilic wicking matrices by capillary forces which can be predicted and analyzed by Lucas-Washburn and Darcy equations.

Although several µPAD fabrication techniques have been reported, each technique has its own drawbacks. For example, µPAD fabrication via wax printing is a simple, rapid, and cost effective method. However, this wax printed µPAD is unstable under high temperature and sensitive to organic solvents which can penetrate through wax barriers. Photolithography technique requires an extra washing step to remove un-crosslinked polymers. Inkjet etching requires the paper substrate to be coated with polystyrene for 2 hours prior to printing to have high stability. Other µPAD fabrication techniques such as flexography printing and screen printing are sensitive to organic solvents as well. In contrast, chemical modification techniques such as inkjet printing using alkyl ketene dimer (AKD) and plasma treatment result in proper solvent resistance since chemical agents effectively couple with hydroxyl groups on cellulose fiber in chromatography paper covalently. However, the plasma treatment requires different masks for creating different microfluidic patterns on a paper and inkjet printing technique requires an extra heating step for eight minutes after AKD deposition. Kwong et al. developed an initiated chemical vapor deposition (iCVD) method to deposit poly (methacrylic acid-co-ethylene glycol dimethacrylate) and poly (methacrylic acid) (PMMA) on a chromatography paper. However, the fabrication process requires more than 15 minutes including multiple washing steps to remove the ungrafted PMMA from the paper substrate.

There is currently a need for cost effective screening devices, especially in third world countries. Despite advances in the art, there remains a need to improve µPAD fabrication and applications therewith.

SUMMARY OF THE DISCLOSURE

It is therefore an object of the present invention to provide a chemical vapor deposition (CVD) method to create a thermally and chemically stable hydrophobic barrier for µPADs which is called "C-µPAD". This C-µPAD fabrication technique requires a chromatography paper, trichlorosilane (TCS) as a hydrophobic agent, and a vacuum chamber to create hydrophobic patterns. The fabrication requires a single step that takes only two minutes to create a C-µPAD. Various C-µPADs were fabricated to show the versatility of this device by demonstrating glucose assay, immunoassay, and heavy metal detection.

In one aspect, a chemically patterned microfluidic paper-based analytical device (C-µPAD) is developed to create fluidic networks by forming hydrophobic barriers using chemical vapor deposition (CVD) of trichlorosilane (TCS) on a chromatography paper. By controlling temperature, pattern size, and CVD duration, optimal conditions were determined by characterizing hydrophobicity, spreading patterns, and flow behavior on various sized fluidic patterns. With these optimal conditions, we demonstrated glucose assay, immunoassay, and heavy metal detection on well-spot C-µPAD and lateral flow C-µPAD.

It is another object of the present invention to provide a simple, fast, and sensitive method for multiplexing heavy metal detection. A microfluidic paper-based analytical device by chemical vapor deposition is thus used for multiplex heavy metal detection in water. Silane compounds such as APTES, TESPSA, and MPTMS that terminated with functional groups (amine, carboxyl and thiol) were covalently attached on the hydroxyl group of the cellulose fiber in a chromatography paper. With these functional groups on µPAD developed, we immobilized the colorimetric reagents of dimethylglyoxime on amine functional group, 1,5-diphenylcarbazide on the carboxyl group and Michler's thioketone on the thiol functional group to detect the Ni, Cr and Hg, respectively. For the analysis, water samples were applied on the μPAD and metal-complex formed uniformly at the detection zone and can measure the concentration quantitatively based on the color intensity. These assay demonstrations proved that the immobilization of functional groups and multiplex heavy metal detection is suitable for real-world applications and established the approach for DNA analysis.

Using a chemically patterned microfluidic paper-based analytical device (C-μPAD), silane compounds terminating in amine (NH2), carboxyl (COOH), and thiol (SH) were immobilized on a patterned chromatography paper via condensation reactions. Three chromogenic reagents that react distinctly with Ni (II), Cr (VI), and Hg (II) were then covalently coupled to these functional groups. The detection limits for this single-plex platform were twice as good as those obtained in previous studies due to the formation of homogeneous metal complexes from immobilized chromogenic reagents. Furthermore, by minimizing cross-reaction with chelating agents and maximizing reaction uniformity, multiplex heavy metal ion detection was successfully demonstrated for lake-water samples spiked with various concentrations of heavy metal ions with high precision. This functionalized C-μPAD provides a highly portable and rapid on-site monitoring platform for multiple heavy metal ions detection with extremely high repeatability, which is useful for resource-limited areas and developing countries.

It is therefore an object of the present invention to provide a method for preparing a chemically patterned microfluidic paper-based analytical device (C-μPAD), comprising: forming one or more hydrophobic barriers by chemical vapor deposition (CVD) of a hydrophobic material on a substrate layer; attaching at least one detection compound having at least one functional group to the hydrophobic material on the substrate layer; and immobilizing onto the functional group at least one chromogenic reagent that reacts to at least one analyte of interest, wherein the one or more hydrophobic barriers are capable of channeling one or more fluids through a channel to detect the presence of the at least one analyte, wherein the at least one chromogenic reagent immobilized on the functional group is capable of visual color change when the at least one analyte is detected by the at least one functional group.

It is another object of the present invention to provide a chemically patterned microfluidic paper-based analytical device (C-μPAD), comprising: one or more hydrophobic barriers by chemical vapor deposition (CVD) of a hydrophobic material on a substrate layer; at least one detection compound attached to the hydrophobic material having at least one functional group; and at least one chromogenic reagent immobilized onto the at least one detection compound, said at least one chromogenic reagent being capable of being reacted to at least one analyte of interest wherein the one or more hydrophobic barriers are capable of channeling one or more fluids through a channel to detect the presence of the at least one analyte, wherein the at least one chromogenic reagent immobilized on the functional group is capable of visual color change when the at least one analyte is detected by the at least one functional group.

It is yet another object of the present invention to provide a chemically patterned microfluidic paper-based analytical device (C-μPAD) for heavy metal detection in water, comprising: one or more hydrophobic barriers by chemical vapor deposition (CVD) of a hydrophobic material on a substrate layer; at least one amine compound immobilized to the hydrophobic material; and at least one chromogenic reagent immobilized onto the at least one amine compound, said at least one chromogenic reagent being capable of being reacted to at least one heavy metal compound of interest, wherein the chromogenic reagent is capable of colorimetric reaction upon the presence of the at least one heavy metal of interest.

It is yet another object of the present invention to provide a method comprising: selecting a microfluidic paper-based analytical device (μPAD), wherein the μPAD comprises one or more hydrophobic barriers of a hydrophobic material deposed on a substrate layer, wherein the one or more hydrophobic barriers define one or more fluidic channels, one or more detection compounds attached to the substrate in the one or more fluidic channels, wherein the one or more detection compounds each have at least one functional group, and one or more chromogenic reagents immobilized onto the one or more detection compounds; channeling a fluid through at least one of the one or more fluid channels, wherein the fluid comes in contact with the one or more chromogenic reagents; and detecting one or more analytes of interest in the fluid based upon a reaction between the one or more analytes of interest and the one or more chromogenic reagent, wherein the detection comprises the one or more chromogenic reagents changing visual color when the one or more analytes of interest react with the one or more chromogenic reagent.

In one aspect the one or more detection compounds are selected from a group consisting of: (3-aminopropyl) triethoxysilane (APTES), triethoxysiloslylpropyl succinic anhydride (TESPSA), (3-Mercaptopropyl) trimethoxysilane (MPTMS), human TNFα biotinylated antibody, straptabividin-HRP reagent, 1-Ethyl-3-(3-dimethylaminopropyl)-carbodiimide (EDC), N-hydroxysuccinimide (NHS), N-hydroxysulfoxuccinimide (sulfo-NHS), and combinations thereof.

In another aspect, the one or more detection compounds comprise an assay reagent. In yet another aspect, the assay reagent is an enzyme selected from a group consisting of o-dianisidine, glucose peroxidase, glucose oxidase, horseradish peroxidase, uricase, amine terminated magnetic particles, carbodiimide coupled enzymes, and combinations thereof.

It is yet another object of the present invention to utilize one or more amine-functionalized silica microparticles which immobilize one or more enzymes. The one or more chromogenic reagents are colorimetric, chemiluminescent, luminescent, or combinations thereof. In another aspect, the one or more chromogenic reagents are selected from a group consisting of: horseradish peroxidase (HRP), dimethylglioxome (DMG), 1,5 diphenylcarbazide, Michler's thioketone, and combinations thereof. The one or more analytes of interest may be glucose, TNFα, respiratory disease markers, HIV, HBV, and metal ions. In another aspect the analytes of interest are one or more heavy metals.

It is yet another object of the present invention to provide a microfluidic paper-based analytical device (μPAD), wherein the μPAD comprises: one or more hydrophobic barriers of a hydrophobic material deposed on a substrate layer defining one or more fluidic channels; a detection compound attached to the substrate in the one or more fluidic channels, wherein the detection compound has at least one functional group; and a chromogenic reagent immobilized onto the detection compound, wherein the one or more hydrophobic barriers define one or more fluidic channels through which a fluid can be channeled so that the fluid comes in contact with the chromogenic reagent, the chromogenic reagent is operable to react with an analyte of interest in the fluid, and the chromogenic reagent is operable to change visual color when the analyte of interest reacts with the chromogenic reagent.

In one aspect the substrate layer comprises chromatography paper. In another aspect, the substrate layer may be chromatography paper, cellulose paper, nitrocellulose acetate, cellulose acetate, filter paper, tissue paper, writing paper, paper towel, cloth, or porous polymer film.

In one aspect the hydrophobic material is trichlorosilane. In another aspect the hydrophobic material is a chlorosilane compound.

In one aspect the one or more detection compounds may be (3-aminopropyl) tri-ethoxysilane (APTES), triethoxysiloslylpropyl succinic anhydride (TESPSA), (3-Mercaptopropyl) trimethoxysilane (MPTMS), human TNFα biotinylated antibody, straptavidin-HRP reagent, 1-Ethyl-3-(3-dimethylaminopropyl)-carbodiimide (EDC), N-hydroxysuccinimide (NHS), N-hydroxysulfoxuccinimide (sulfo-NHS), and combinations thereof. In another aspect the one or more chromogenic reagents can be: horseradish peroxidase (HRP), dimethylglioxome (DMG), 1,5 diphenylcarbazide, Michler's thioketone, and combinations thereof.

It is yet another object of the present invention to provide a method for preparing a chemically patterned microfluidic paper-based analytical device (C-μPAD), comprising: forming one or more hydrophobic barriers by chemical vapor deposition (CVD) of a hydrophobic material on a substrate layer defining one or more fluidic channels; attaching a detection compound having at least one functional group to the substrate in the one or more fluidic channels on the substrate layer; and immobilizing onto the functional group one or more chromogenic reagents, wherein: the one or more hydrophobic barriers define one or more fluidic channels through which a fluid can be channeled so that the fluid comes in contact with the one or more chromogenic reagents, the one or more chromogenic reagents are operable to react with one or more analytes of interest in the fluid, and the one or more chromogenic reagents are operable to change visual color when the one or more analytes of interest react with the one or more chromogenic reagent.

In one aspect the one or more detection compounds can be: (3-aminopropyl) tri-ethoxysilane (APTES), triethoxysiloslylpropyl succinic anhydride (TESPSA), (3-Mercaptopropyl) trimethoxysilane (MPTMS), human TNFα biotinylated antibody, straptavidin-HRP reagent, 1-Ethyl-3-(3-dimethylaminopropyl)-carbodiimide (EDC), N-hydroxysuccinimide (NHS), N-hydroxysulfoxuccinimide (sulfo-NHS), and combinations thereof. In another aspect the one or more detection compounds comprise an assay reagent. The assay reagent can be: o-odianisidine, glucose peroxidase, glucose oxidase, horseradish peroxidase, uricase, amine terminated magnetic particles, carbodiimide coupled enzymes, and combinations thereof.

In another aspect, the method further utilizes one or more amine-functionalized silica microparticles which immobilize one or more enzymes. The one or more chromogenic reagents are colorimetric, chemiluminescent, luminescent, or combinations thereof. The one or more analytes of interest can be: glucose, TNFα, respiratory disease markers, HIV, HBV, and metal ions. In another aspect the one or more analytes of interest are one or more heavy metals.

BRIEF DESCRIPTION OF THE DRAWINGS

The foregoing and other objects, features, and advantages of the disclosure are apparent from the following description of embodiments as illustrated in the accompanying drawings, in which reference characters refer to the same parts throughout the various views. The drawings are not necessarily to scale, emphasis instead being placed upon illustrating principles of the disclosure:

FIG. 1A-D depicts development of paper-based microfluidic platform using C-μPAD technique. (FIG. 1A) Schematic illustration of fabrication process: A vinyl tape was cut based on a designed CAD file and then transferred onto 4.5×5 cm chromatography paper. The patterned paper was placed into the vacuum chamber with 100 μL of TCS solution placed on a 53° C. heat block. After vacuum process, the tape was removed and fluidic pattern was ready for bioassay. (FIG. 1B) and (FIG. 1C) Positive and negative features of 2 dimensional channels on C-μPAD (FIG. 1D) Demonstration of a multi-layered C-μPAD including top layer (TTU letters) and bottom layer (interconnection channels between letters).

FIG. 2A-C depicts characterization of C-μPAD technique by controlling CVD duration and channel area (FIG. 2A) Front side of the patterned chromatography paper at 30 seconds of CVD duration. (FIG. 2B) Back side of the patterned chromatography paper at 30 seconds of CVD duration. (FIG. 2C) Different dimensions of channels (4, 3, 2, 1, 0.5 mm width×10 mm length) were analyzed with different CVD duration (20, 25, and 30 seconds).

(FIG. 3A-3F) Red dye color solution was applied onto both untreated chromatography paper and treated paper-based microfluidic device to demonstrate the different time point flow rate. (FIG. 3G) The distance that red dye color travels inside the channel of C-μPAD in terms of time was then compared with the data of fluid flows in a normal chromatography paper.

(FIG. 4A) Different concentrations of glucose solutions from 0 to 160 mg/dL were applied onto each spot on a well-spot C-μPAD. (FIG. 4B) Glucose assays with various concentrations of glucose from 0 to 160 mg/dL were analyzed on lateral flow C-μPAD. Assay reagents were added into the reaction zone, the other end of channel allowed to flow glucose solution freely into the reaction zone. (FIG. 4C) This plot shows a linear relationship between various concentrations of glucose and their differential gray intensity in lateral flow C-μPAD. (FIG. 4D) Front side of C-μPAD after extracting plasma separation from the human blood. Each spot shows similar color since each glucose-spiked sample uses the same amount of blood. (FIG. 4E) Well-spot glucose assays from various concentrations of glucose-spiked blood samples. (FIG. 4F) Glucose assay results on the well-spot C-μPAD using standard glucose samples and glucose-spiked whole blood samples. These results show a strong linear relationship between glucose concentrations and gray intensity.

(FIG. 5B) C-μPAD shows a clear concentration gradient after the assay with different concentration of TNFα (0 ng/mL~1,000 ng/mL). (FIG. 5C) Immunoassay results acquired by a smartphone camera and analyzed by image J software. These results show log-linear relationship between TNFα concentrations and differential gray value.

FIG. 6A-D depicts (FIG. 6A) Immobilization of amine functional group on "Ni" symbol patterned C-μPAD (FIG. 6B) Ni detection on "Ni" symbol patterned C-μPAD (FIG. 6C) Various concentrations of Ni on the well-spots C-μPAD (FIG. 6D) A standard curve for Ni detection. Gray intensity increases with a log-linear relationship with concentration of Ni.

(FIG. 8A) Various concentrations of amine, carboxyl, and thiol functionalized on the well-spot array of the C-µPAD. The amine functional group was confirmed using ninhydrin as a reagent. Litmus was the reagent for carboxyl, and Elmann's reagent was the reagent for thiol; these reactions produced orange and yellow colors, respectively, which varied with the concentration. (FIG. 8B) Euclidean distances between shades of red, green, and blue for each concentration. Silane compounds above 3% reached the saturation point.

FIG. 9A-F depicts demonstration of the quantitative analysis conducted during heavy metal detection using the surface-modified well-spot C-µPAD. (FIG. 9A-C) Two-fold serial dilutions of Ni (II), Cr (VI), and Hg (II) from 20 to 0.03 ppm were conducted on each spot Colorimetric changes between heavy-metal concentrations were measured using the RGB value in ImageJ. (FIG. 9D-F) A calibration curve for 0-to-20 ppm samples of Ni (II), Cr (VI), and Hg (II) was generated by measuring the Euclidean distances between the RGB colors formed on the surface-modified well-spot C-µPAD.

FIG. 10A-E depicts specificity analysis: (FIG. 10A-D) 10 ppm samples of Ni (II), Cr (VI), and Hg (II) were tested using the 3×3-matrix C-µPAD. These colorimetric assays were specific and showed no interferences from other colorimetric reagents. (FIG. 10E) Data representing the Euclidean distances between the RGB colors formed in the control and test well-spot C-µPADs.

FIG. 11A-J depicts heavy metal detection for standard and spiked lake-water samples using the multiplex C-µPAD pattern. (FIG. 11A) Heavy metal ion samples applied to the detection zone in the multiplex assay. (FIG. 11B-E) Multiplex heavy metal assays in which samples containing DI water and either 5 ppm of NI (II), 5 ppm of Cr (VI) or 0.3 ppm of Hg (II) were applied via the sample inlet. (FIG. 11F-I) Each heavy metal ion was spiked into lake-water samples for the multiplex heavy metal detection, and uniform color development was obtained on the designed detection zones. (FIG. 11J) Histograms were obtained from figure e, showing the distribution of grayscale with normalized intensity.

FIG. 12A-B depicts colorimetric assays showing heavy metal detection on the letters. (FIG. 12A) Ni (II) detection on the surface modified C-µPAD letter pattern. (FIG. 12B) Cr (VI) detection on the surface modified C-µPAD letter pattern.

(FIG. 15A) 0.5 ppm on µPAD VS 5 ppm of Ni (II) and Cr (VI) and 0.3 ppm of Hg (II) on C-µPAD, (FIG. 15B) 0.5 ppm on µPAD VS 0.6 ppm on C-µPAD (FIG. 15C) The distribution of pixels among 8-bit grayscale from $SiO_2$ nanoparticles-modified µPAD.

DETAILED DESCRIPTION OF THE DISCLOSURE

Figure 3G:
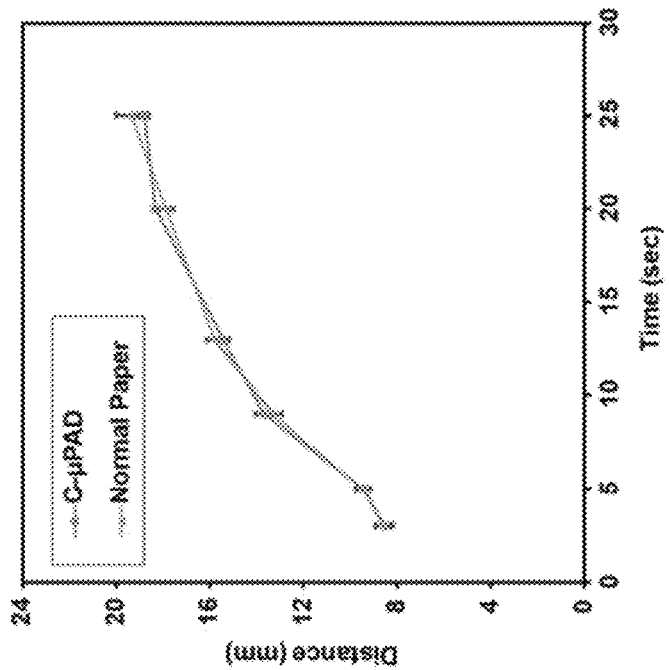
FIG. 3A-G depicts distance vs. time analysis on normal chromatography paper and patterned fluidic device with red dye solution.
Figure 3A:
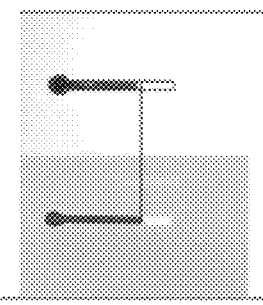
Figure 3B:
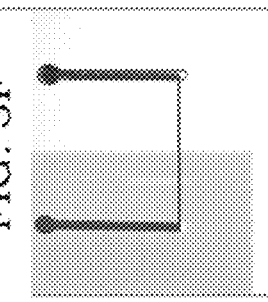
Figure 3C:
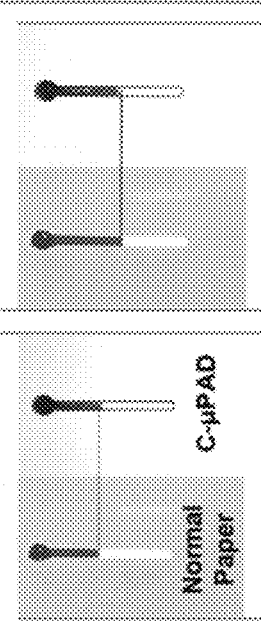
Figure 3D:
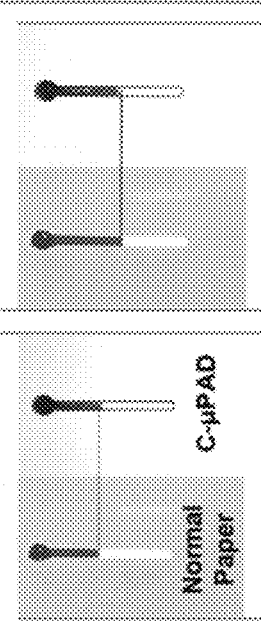

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Turning to the present invention, advances in technology have allowed the human race to detect viruses, bacteria, and harmful environmental chemicals more precisely. However, the methods used to perform these tasks require highly specialized personnel and expensive equipment. In analysis of proteins and enzymes, microfluidic design has proven to be a powerful technological tool to improve performance of immunoassays, enzymatic reactors, and other biological assays. Importantly, manipulation of liquid inside microscale fluidic networks enables reduced consumption of reagents, compared to macroscale instruments.

Microfluidics is a multidisciplinary field intersecting engineering, physics, chemistry, biochemistry, nanotechnology, and biotechnology, with practical applications to the design of systems in which low volumes of fluids are processed to achieve multiplexing, automation, and high-throughput screening. Microfluidics emerged in the beginning of the 1980s and is used in the development of inkjet printheads, DNA chips, lab-on-a-chip technology, micro-propulsion, and micro-thermal technologies. It deals with the behavior, precise control and manipulation of fluids that are geometrically constrained to a small, typically sub-millimeter, scale. Typically, micro means one of the following features: (i) small volumes (μL, nL, pL, fL), (ii) small size, (iii) low energy consumption, and (iv) effects of the micro domain.

Typically fluids are moved, mixed, separated or otherwise processed. Numerous applications employ passive fluid control techniques like capillary forces. In some applications external actuation means are additionally used for a directed transport of the media. Examples are rotary drives applying centrifugal forces for the fluid transport on the passive chips. Active microfluidics refers to the defined manipulation of the working fluid by active (micro) components such as micropumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reducing sample and reagent volumes.

Microfluidic structures include micropneumatic systems, i.e. microsystems for the handling of off-chip fluids (liquid pumps, gas valves, etc.), and microfluidic structures for the on-chip handling of nano- and picolitre volumes. To date, the most successful commercial application of microfluidics is the inkjet printhead. Significant research has also been applied to microfluidic synthesis and production of various biofunctionalized nanoparticles including quantum dots (QDs) and metallic nanoparticles, and other industrially relevant materials (e.g., polymer particles). Additionally, advances in microfluidic manufacturing allow the devices to be produced in low-cost plastics and part quality may be verified automatically. An emerging application area for biochips is clinical pathology, especially the immediate point-of-care diagnosis of diseases. In addition, microfluidics-based devices, capable of continuous sampling and real-time testing of air/water samples for biochemical toxins and other dangerous pathogens, can serve as an alarm for early warning. Microfluidic devices may be continuous-flow, chip-based, droplet-based, digital, microarrays, optics, acoustic droplet injection, fuel cells and the like.

Decreased liquid volume and short diffusion lengths allow facile reactions between analyte and antibody or enzyme and substrate, resulting in reduced assay times with microfluidic assays. Over the past decade the interest in paper-based micro fluidics has risen significantly. Currently, wax printing is the most popular fabrication method due to its high throughput and channel precision as low as 600 microns. This method is susceptible to heat which can distort the wax barrier and compromise the channel, and the cost of the wax printer is relatively high. The present invention present an improved chemical patterning technique that is unaffected by heat which is required for certain applications, and does not require expensive printers.

In one embodiment a during C-μPAD fabrication, hydrophobic barriers were achieved by CVD process of TCS as shown in FIG. 1(A) to silanize a chromatography paper. A vinyl tape 101 is cut with a cutting plotter, which may be controlled by a processor, a designed pattern 102. The vinyl tape cut into the pattern 102 is then superimposed on chromatography paper 103. The vinyl tape-treated chromatography paper 105 is then subjected to; the reaction takes place readily with TCS vapor 104 and requires a low-pressure chamber and heat block as a source of heat supply. In this exemplary embodiment, vaporized TCS molecules 104 from CVD process penetrated through the paper to form covalent bonds with hydroxyl groups on cellulose fibers that provide extremely stable and highly reproducible hydrophobic barriers. TCS is a highly volatile compound which has 594 mmHg of vapor pressure at 25° C. The deposition of TCS molecules is strongly dependent on pressure, CVD duration, temperature, volume of TCS, and the mobility of the molecules. By controlling the duration and temperature in the CVD process, the chemical molecules will travel through the chromatography paper and immobilize uniformly throughout the paper. Thus, different CVD duration and temperature were followed to find the optimum. After CVD processes with different durations, contact angle measurement was used to demonstrate the strength of hydrophobic barrier of TCS. Previous studies demonstrated that the contact angle of the water droplet on a highly hydrophobic filter paper was 110~125'31, 32. In the C-μPAD fabrication process, the relationship of contact angle and the CVD duration was proportional until reaching the saturation point. The hydrophobicity of the C-μPAD surface was observed by an increase in the contact angle. From 0 to 10 minutes of the CND duration, the contact angle was 115° at 30 seconds and reached the saturation point of approximately 125° after 10 minutes. Moreover, the contact angle measurement ensured the quality and reproducibility of various C-μPADs. Hence, well-controlled hydrophilic barrier could be created by mainntaining a standard contact angle. Based on our results, the contact angle of 115° on the top side of the pattern was stable and strong enough to carry out the bioassay. Following treatment, the TCS or chlorosilane compound is deposited on the remaining chromatography paper 106 with the exception of the fluidic pattern 107 remaining after the removal of the vinyl tape 101. After the C-μPAD fabrication process, silanized hydrophobic patterns are invisible to the eyes and the modified area retains its original flexibility. FIG. 1(B-D) shows various C-μPAD patterns on chromatography paper with food dyes. The patterns show both single layered C-μPAD with multiple color depositions and double layered C-μPAD. These C-μPADs exhibited the well-defined hydrophobic borders to wick uniformly throughout the hydrophilic paper networks. In addition, the aforementioned CVD process can be extended to fabricate the C-µPAD on other types of paper without any significant modification.

Optimal CVD duration with various sized rectangle patterns was characterized to determine resolution of this C-µPAD fabrication technique. FIG. 2 shows the result of this experimental characterization. FIGS. 2A and 2B present the front and back side of the patterned papers. Both sides formed the proper hydrophobic barriers without any spreading issues. FIG. 2C shows the relationship between channel area and CVD duration for the respective channel size. As shown in FIG. 2C, 30 seconds CVD duration at 53° C. is the best fit with the ideal case which is the same hydrophilic area for both front and back side of the patterned paper. For CVD durations longer than 30 seconds, the hydrophilic area decreased because the hydrophobic reagent penetrated the hydrophilic barrier under the vinyl tape patterns. For CVD durations shorter than 30 seconds, the spreading degrees on both sides were larger than the original area since the vaporized TCS molecules could not penetrate through the paper completely to form hydrophobicity on the back side of the paper. From this characterization, with 30 seconds CVD duration at 53° C., the C-µPAD enabled us to fabricate as low as 500 µm width channel with the best hydrophilic and hydrophobic contrast. This fabrication limit is due to aspect ratio of channel width and paper thickness under penetration speed of vaporized TCS molecules. Using current chromatography paper, we achieved aspect ratio up to 0.4 on the 200 µm thick chromatography paper. Random mobility of TCS vapor molecules in vacuum chamber results in relatively low aspect ratio. The aspect ratio of this fabrication method can be improved by choosing a thinner paper having high density of hydroxyl functional groups.

Figure 3E:
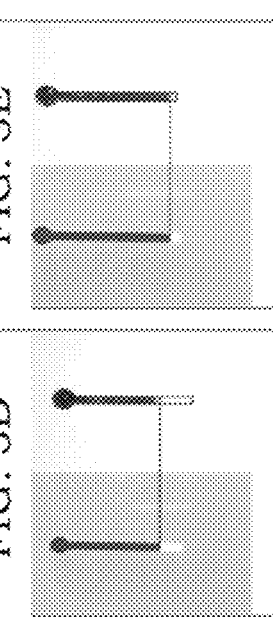
Figure 3F:
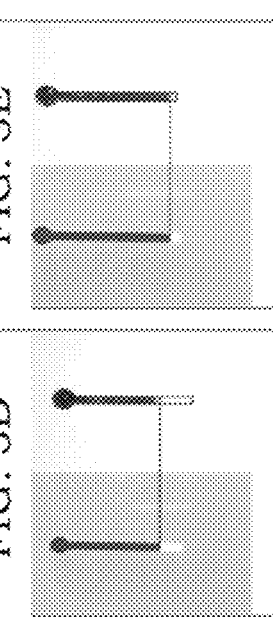

The flow velocity of C-µPAD was compared with that of a normal chromatography paper. During the CVD process, vaporized TCS molecules can penetrate from the top or side of masking film. This unwanted exposure influences the wicking properties of the paper which alters fluid transport properties of the C-µPAD. FIG. 3A-D shows the difference between fluid velocities in a normal chromatography paper and the C-µPAD. There was only ~5% variation for overall velocities as shown in FIG. 3E. This much variation can originate from paper itself since the internal structure of chromatography paper consists of highly heterogeneous fiber directions, pore size, and pore distribution.

CVD duration was characterized by measuring contact angle on hydrophobic area of the paper and the patterned channel size of C-µPAD. To characterize hydrophobicity of the exposed paper with respect to CVD duration, a quarter of original chromatography paper (11 cm×11 cm) was fabricated by CVD method for times varying from 10 seconds to 60 minutes. After CVD treatment, each treated paper was cut and fixed onto a slide glass for the contact angle measurement using a goniometer (West Scientific). 5 µL of DI water was dropped on the surface of each treated paper to measure the contact angle.

In addition, the relationship between CVD duration and fabrication resolution of the C-µPAD was investigated. At first, rectangular channel patterns with dimensions of 4, 3, 2, 1, and 0.5 mm in width with 10 mm in length were prepared with the vinyl cutter and performed CVD process with CVD duration of 20, 25, and 30 seconds. After processing this fabrication, food dye solution was applied on each channel to determine total spreading area on front and back side of the channel in each CVD duration. Furthermore, flow velocity within the hydrophilic channel was characterized and compared with an intact chromatography paper. A C-µPAD was created with a 20 mm dumbbell-shaped channel and a similar shape was cut on a chromatography paper using the vinyl cutter. Food coloring dye solution was applied onto both C-µPAD and normal chromatography paper at the same time, and a videotape was recorded in order to compare the flow velocity with each other.

EXAMPLES

1. Glucose Assay.

Figure 4A:
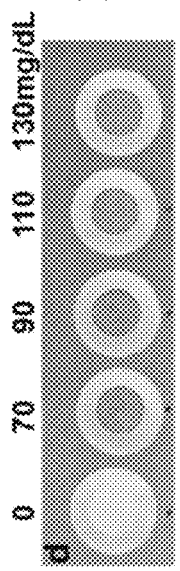
FIG. 4A-F depicts demonstration of glucose assay on well-spot C-μPAD and lateral flow C-μPAD.

To show bioassay capabilities of C-µPAD, glucose assays were demonstrated on well-spot C-µPAD and lateral flow C-µPAD platforms using standard glucose samples. FIG. 4A shows that color intensity increases as glucose concentration increases from 0 to 160 mg/dL in glucose well-spot C-µPAD. Based on the LOD calculation, 13 mg/dL of LOD was achieved in well-spot C-µPAD, which is equivalent to the LOD of the commercially available glucose meter (AccuCheck). Furthermore, a lateral flow glucose assay was developed by using a dumbbell-shaped channel. A lateral flow glucose assay using lateral flow C-µPAD was developed to demonstrate the additional step of sample transport to the spotted detection reagents. A lateral flow C-µPAD with dumbbell-shaped patterns was created for this lateral flow glucose assay. 5 µL of assay reagent was physically immobilized and dried onto reaction wells. 2.5 µL of various concentration of glucose solutions such as 0, 40, 80, 120, and 160 mg/dL was then dropped onto the sample inlet and allowed to flow freely to each reaction well. After 10 minutes, oxidized o-dianisidine produced brown color at reaction well depending on the glucose concentration. The aforementioned process was followed to measure the gray intensity. Furthermore, the standard glucose assay was performed in a 96-well plate for comparison with the glucose assay on C-µPAD. For this standard assay, the same concentrations with the lateral flow C-µPAD were tested by following a commercial protocol (Sigma Aldrich glucose assay kit) and analyzed by microplate reader (Genesys, Tecan).

Figure 4B:
Figure 4C:
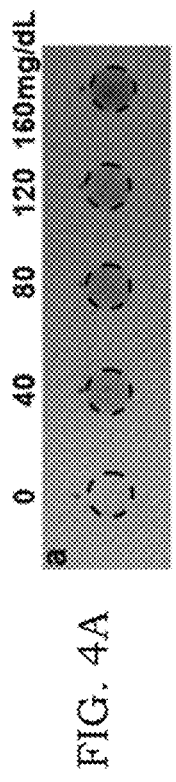

In the reaction zone of the lateral flow C-µPAD, 5 µL of assay reagent was immobilized by spotting 4 times since the reaction zone can accommodate only 1.25 µL. For a glucose assay using the lateral flow C-µPAD, 2.5 µL of glucose sample was then applied on the sample inlet, allowed to flow, and reacted in the detection zone. FIG. 4B shows the gradient of color intensity depending on the glucose concentration. FIG. 4C clearly indicates the differences between the color intensity for each concentration of glucose in lateral flow C-µPAD. The lateral flow assay was successfully demonstrated with the same range of glucose concentration with well-spot C-µPAD glucose assay and 23 mg/dL of LOD was achieved. For the well spot assay, D-(+)-Glucose powder was dissolved in deionized (DI) water and serially diluted to prepare 0~160 mg/dL concentration of a standard glucose solution. Then, the combination of glucose oxidase/peroxidase and o-dianisidine was prepared to serve as the assay reagent. 5 µL of assay reagent was physically immobilized and dried onto each well of well-spot C-µPAD. 1 µL of standard glucose solutions with various concentrations was then applied on each well-spot. After 10 minutes, oxidized o-dianisidine produced brown color on each well depending on the glucose concentration. Optical images of this well-spot glucose assay were converted to the 8-bit gray scale and gray intensity of each well was measured by imageJ. All well-spot data was adjusted with background (0 mg/dL) to obtain the absolute values. For a whole blood glucose assay, D-(+)-Glucose powder was dissolved in phosphate-buffered saline (PBS) and serially diluted for various concentration of 0 mg/dL, 40 mg/dL, 80 mg/dL, and 120 mg/dL and then spiked into 140 mg/dL of human whole blood with the volume ratio of 1:1. 5 µL of assay reagent was physically immobilized on each well of well-spot C-µPAD and allowed to dry in the room temperature. 2.5 mm in diameter of Vivid Plasma Separation GX membrane was soaked with PBS and dried in the room temperature before assembly. The dried plasma separation membrane was then attached on each well spot with a vinyl ring-shaped tape. 3 µL of each spiked blood sample was applied on each membrane to quantify glucose level. After 5 minutes, brown color spot was observed on back side on the each well and gray intensity of each well was analyzed as the aforementioned procedure.

To determine the correlation between 96-well plate and lateral flow C-µPAD methods, results from both measurements were compared. Lateral flow C-µPAD data has a good agreement with the standard 96-well plate assay measured by spectrophotometer. Even though the same concentration of glucose was used for both well-spot C-µPAD and lateral flow C-µPAD, the well-spot C-µPAD showed higher color intensity. For well-spot C-µPAD, there was no volume loss since all applied glucose samples reacted with immobilized assay reagents. For lateral flow C-µPAD, 2.5 µL of glucose sample was applied on the sample inlet, which had to flow through the channel to reach the reaction zone. From volume calculation, ~0.8 µL of glucose samples reacted with the immobilized assay reagents.

Figure 4D:
Figure 4E:
Figure 4F:
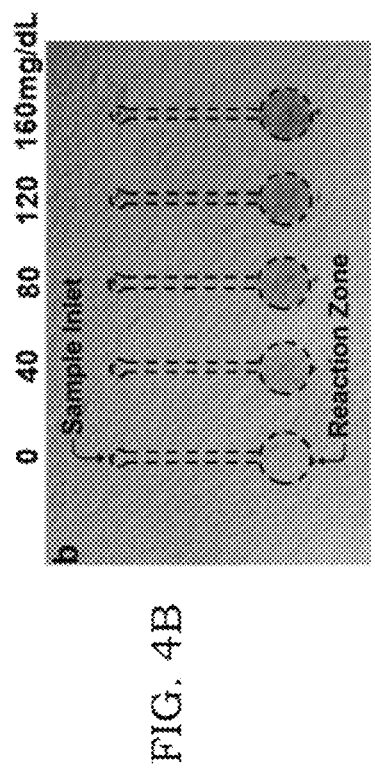

To demonstrate the C-µPAD ability for point-of-care diagnostics (POC), a human blood glucose assay on well-spot C-µPAD was conducted. A plasma separation membrane (Pall Corporation) was fixed on the front side of the well-spot C-µPAD to extract plasma from the blood shown in FIG. 4D. FIG. 4E shows the assay results on the back side of the well-spot C-µPAD from glucose-spiked blood samples. As expected, overall color intensity increases as the total amount of glucose increases from glucose-spiked blood samples. Compared to the standard well-spot glucose assay in FIG. 4F, the color intensities from the blood samples are less than those of the standard glucose samples due to differences in fluidic properties and mild reaction inhibitors in the extracted plasma. Even overall intensity is shifted down a bit, sensitivity from the blood samples is almost identical with that from the standard glucose samples.

2. Immunoassay.

Figure 5B:
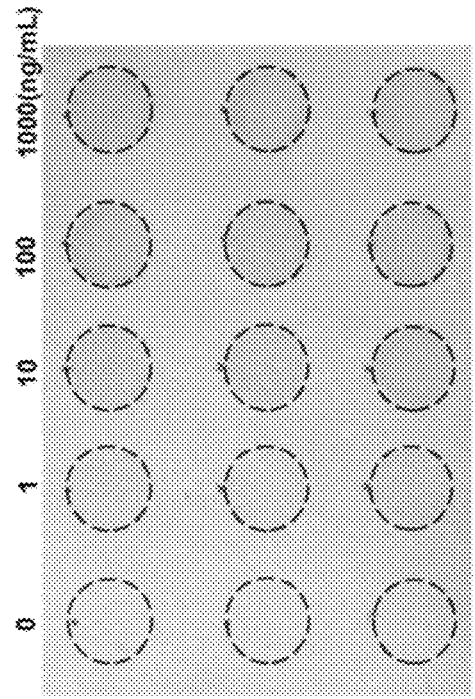
FIG. 5A-C depicts (FIG. 5A) Procedure of immunoassay on C-μPAD.
Figure 5C:
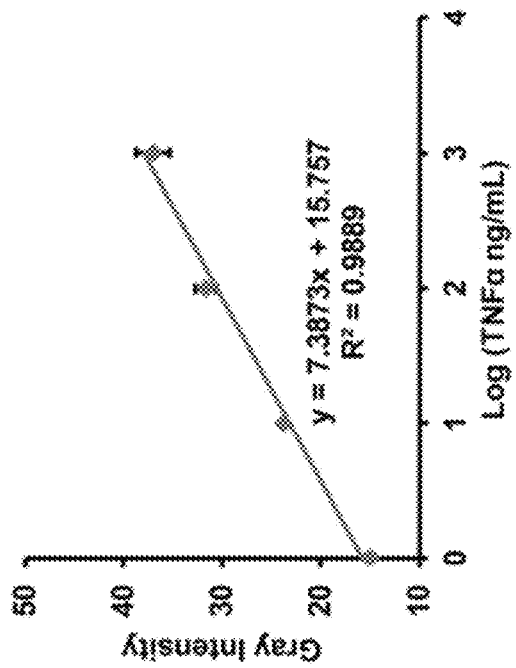
Figure 5A:
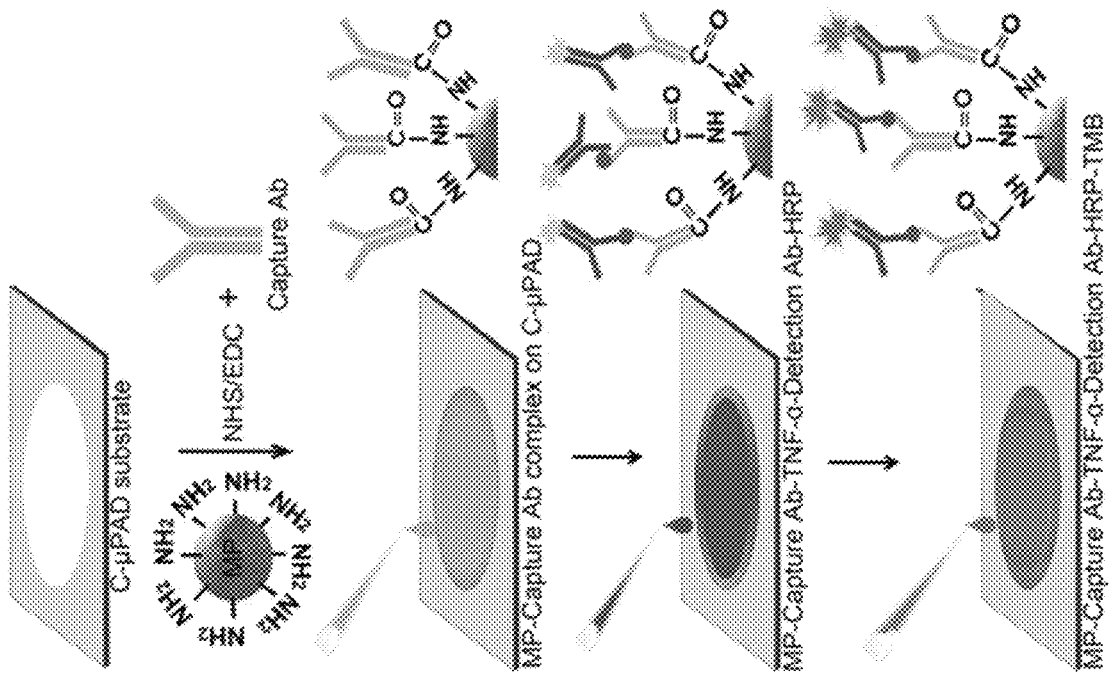

In addition to glucose assays, a sandwich immunoassay for TNFα quantification was demonstrated on well-spot C-µPAD by following the procedure shown in FIG. 5A. 1 µm sized amine terminated magnetic particles was suitable to apply on the well-spot C-µPAD since the pore size of the paper is in the range of ~1 µm and can physically trap the beads. EDC/NHS was used to activate the carboxyl group of human anti-TNFα capture antibody that would lead to covalent conjugation between human anti-TNFα antibody and amine-terminated magnetic particles. The immune complex was formed on the amine functionalized magnetic particles.

A well-spot C-µPAD was developed with 4 mm in diameter well-spot array pattern. For the immunoassay, 1 µg/mL TNFα antibody was incubated with 1 µg/mL of EDC/NHS for 30 minutes and applied on the 1 µm size of amine functionalized magnetic particles. The magnetic particles were physically immobilized on the well-spot C-µPAD. 1 µL of various concentrations including 1, 10, 100, and 1000 ng/mL of human TNFα was then applied on each well-spot and incubated for 10 minutes. Then, 1 µg/mL of human TNFα biotinylated antibody, and followed by 2 µL of streptavidin-HRP reagents was applied on the substrate; again, the substrate was incubated for 10 minutes at room temperature. Subsequently, the well-spot C-µPAD was placed into a petri dish, covered in 500 µL of PBS, and rinsed 2 times to remove unbound proteins. Further, the spots were dried using laboratory wipes. 2 µL of TMB substrate was then applied on each spot and incubated for 10 minutes to induce the peroxidase reaction. 2 µL of TMB stop solution was then added in each spot to stop the reaction that produced yellow color based on the antigen concentration. For a negative control, 1% of BSA solution was immobilized on the amine-terminated magnetic particles instead of TNFα and their respective antibodies. Finally, TMB solution was applied on the control spot. Furthermore, gray intensity of each well was analyzed using ImageJ after acquiring high resolution photographs and converting to gray scale.

On positive well-spot, the appearance of blue color confirmed the formation of immune complex. Further, TMB stop solution interrupted the reaction which would lead color changes from blue to yellow as shown in FIG. 5B. The intensity of yellow color developed in each well-spot was proportional to the amount of TNFα formed on the well-spot C-µPAD. FIG. 5C shows a log-linear correlation for various concentrations of TNFα demonstrating that the color intensity increased to the concentration ranges of 1~4000 ng/mL. From this TNFα immunoassay demonstration, 3 ng/mL of LOD was achieved under well-spot C-µPAD. This result of immunoassay in well-spot C-µPAD is less sensitive than conventional ELISA. However, in conventional ELISA techniques, larger volume of analytes and reagents including long incubation due to the diffusion limit are required. Compared to the traditional ELISA, C-µPAD decreased the reaction time significantly since this C-µPAD offered 3-dimensional matrix to create immune complex by transporting all liquid samples with wicking force. Furthermore, less than 15 µL of total reagents was sufficient to carry out this sandwich immunoassay on well-spot C-µPAD. Based on this concept, the C-µPAD can be implemented for the detection of cardiovascular disease markers, respiratory disease markers, HIV, HBV, etc., using blood or saliva with POC diagnostic approach. As well, the requirements of small reagent volume, rapid analysis, portable, multiplex detection and low cost are the important qualities to POC diagnostics in both developed and developing countries.

3. Heavy Metal Detection.

Heavy metals are major water contaminants because they bind easily to vital cellular components, accumulating in the organs and contributing to serious diseases, disorders, and organ failures. To prevent water contamination and to monitor water quality, a highly sensitive sensor is required. Atomic absorption spectroscopy (AAS), inductively coupled plasma/atomic emission spectrometry (ICP/AES), inductively coupled plasma mass spectrometry (ICP-MS), and wet chemical methods such as colorimetry, titrimetry, and gravimetry are currently available. However, these techniques are expensive, time-consuming and require established laboratories with skilled technicians. Recently, various sensor detection techniques have been developed for heavy metal detection, including optical sensors, chemiluminescent sensors, electroluminescent sensors, and micro/nanofabricated electrochemical sensors. Though these detection techniques show excellent sensitivity, these systems require complicated synthesis processes and laborious and expensive micro/nanofabrication.

A microfluidic-paper-based analytical device (µPAD) has recently gained prominence as a means of detecting heavy metals because this µPAD provides a highly portable, disposable, and expandable platform for rapid and sensitive heavy metal detection. Two different approaches for detecting heavy metals with μPADs are: (1) enzymatic detection using a bioactivated solid-phase paper sensor and (2) colorimetric assay using a PEG-400-treated μPAD. Due to heterogeneous color development across detection zones, however, quantitative heavy metal detection via colorimetric assay is limited. Some techniques for resolving this issue include flow-fluid control, paper oxidation, and the incorporation of functionalized nanomaterials. Fluid-flow control has been achieved by altering the widths of the channels in the μPAD, carving their surfaces, and polyelectrolyte treated surfaces. Reducing the wicking velocity through channel width modulation enables the reagents to distribute uniformly across the detection zones. This strategy requires controlling the channel dimensions via precise microfabrication (depending on each analysis), which limits the applicability of μPADs. The oxidation method is also utilized to achieve color uniformity across detection zones. By using sodium periodate to oxidize hydroxyl to aldehyde groups, various enzymes (such as glucose oxidase, horseradish peroxidase, and uricase) were successfully immobilized through carbodiimide coupling onto the cellulose substrate for glucose and uric acid assays. However, this oxidized paper fails to show uniform color development in complexometric assays due to interferences from the oxidized surface. Functionalized micro/nanoparticles were used to improve reaction uniformity, which increases detection sensitivity. Amine-functionalized silica microparticles and nanoparticles were used to immobilize the enzymes to increase the homogeneity of the color development across the detection zones. Although these methods have notably improved analytical performance, they are not widely applicable and require specific chemically and thermally stable functionalization processes for grafting various functional groups to μPADs using additional micro/nanoparticles.

In one embodiment, heavy metal detection on C-μPAD was demonstrated on both well-spot and chemical symbol patterned C-μPAD. Nickel (Ni) is one of the heavy metals that could enter into the environmental water through mining, industrial activities, and leaching from wastes. Generally, colorimetric reagents of heavy metal detection spread easily towards the edge of reaction zone on the μPADs which generate cross-reaction and poor detection sensitivity. To resolve this critical problem, we performed amine functionalization on the patterned C-μPAD with APTES by condensation between APTES and OH groups of cellulose fibers on the chromatography paper.

Immobilization of the Amine Functional Group by Thermal Condensation

Chemical symbol "Ni" and well-spot patterned C-μPADs were created using CVD process shown in FIG. 1. 1.5 μL of 3% (3-aminopropyl) tri-ethoxysilane (APTES) was then applied on the patterned chemical symbol and well-spot area and heated at 95° C. for condensation. These C-μPADs were then washed with DI water to remove the unbound APTES and gently dried on a hot plate at 50° C. After these functionalization steps, amine immobilization was confirmed by a standard ninhydrin colorimetric test.

Nickel Detection on Thermally Stable C-μPAD

On amine-modified chemical Symbol "Ni" and 4 mm diameter well-spot C-μPAD, 2 μL of colorimetric reagent (10 mg/mL of Dimethyl glyoxime (DMG) in 50% Ethanol) was applied on the amine functionalized area of the C-μPAD. These C-μPADs were then heated at 65° C. for dehydration. On the "Ni" patterned C-μPAD, 5000 μg/L of NiSO4 was applied to confirm the colorimetric reaction. On spot-well patterned C-μPAD, various concentrations of NiSO4 (5000 μg/L, 2500 μg/L, 1250 μg/L, 600 μg/L, 300 μg/L, 150 μg/L, 0 μg/L (DI water)) were applied on each well on the C-μPAD to obtain a standard curve. All color intensity measurement and analysis methods are the same with previous assays.

Amine functionalization on the "Ni" patterned C-μPAD was then confirmed by a standard ninhydrin test. As shown in FIG. 6A, bluish-purple color was developed only on the letter "Ni" and hydrophobic barrier on the C-μPAD was maintained well even after heating at 95° C. Generally, the most common fabrication for μPAD is to use a wax printing technique which is thermally unstable above 60° C.22. For the common μPAD, selective silane functionalization will be extremely challenging due to thermal instability of printing material. Using this unique property of C-μPAD, Ni detection was demonstrated on amine functionalized well-spot C-μPAD by coupling dimethylglyoxime (DMG). DMG is a colorimetric reagent which can be covalently attached on the amine functionalized C-μPAD and reacted with nickel to form DMG-Ni complex presented in FIG. 6B. By adding various concentration of Ni solution, color intensity is proportional to concentration of Ni as shown in FIG. 6C. A standard curve of Ni detection is presented in FIG. 6D. From this Ni detection demonstration, we were able to detect as low as 150 μg/L of Ni concentration which shows two folds improvement with the previous report36, 37. This heavy metal assay demonstration proves that the C-μPAD enables us to use for silane functionalization which requires thermal condensation to form covalent bonds. In addition, hydrophobicity on the C-μPAD was extremely stable since the TCS molecules altered wetting property of cellulose fibers in the chromatography paper. To estimate overall shelf-life of the C-μPAD, the patterned C-μPADs were stored at ambient conditions for more than six months. There is no significant alteration on hydrophobic barriers for maintaining fluidic patterns on the patterned C-μPADs.

In another embodiment, silane coupling is demonstrated to immobilize three functional groups—amine ($NH_2$), carboxyl (COOH), and thiol (SH)—on a chemically patterned μPAD (C-μPAD) for real-time heavy metal detection. As previously reported, a C-μPAD was used to create a thermally and chemically stable hydrophobic pattern on chromatography paper. Using the patterned paper, a condensation reaction was used to immobilize each of the three functional groups. Then, the colorimetric reagents—dimethylglyoxime, 1,5 diphenylcarbazide, and Michler's thioketone—were covalently coupled to these functional groups to detect Ni (II), Cr (VI) and Hg (II), respectively. The formation of colored metal complexes confirmed the presence of the metal ions in various water samples, and quantitative analyses were conducted to determine the concentrations of each heavy metal by using color intensities with excellent uniformity. Additionally, multiplex heavy metal detection was achieved when lake samples were monitored in real time. Color intensity was used to precisely quantify the concentrations of the heavy metals with excellent repeatability. This in situ surface modification of a C-μPAD provides a reliable analytical tool for point-of-care diagnostics, environmental monitoring, and chemical and bioanalytical applications in low-resource settings.

Materials and Methods, Chemicals and Solutions:

Trichlorosilane (TCS) (97%); (3-Aminopropyl) triethoxysilane (APTES); triethoxysilylpropyl succinic anhydride (TESPSA); (3-Mercaptopropyl) trimethoxysilane (MPTMS); ninhydrin reagent; litmus reagent; Ellman's reagent; and metal ions of $NiSO_4$, $K_2C_2O_7$, and $HgCl_2$ and their respective colorimetric reagents (Dimethylglyoxime, 1,5-Diphenylcarbazide, and Michler's thioketone) were purchased from Sigma Aldrich. Ethylenediaminetetraacetic acid (EDTA) and all other analytical-grade reagents were also purchased from Sigma Aldrich, Whatman No. 1 chromatography paper (Carolina Biological, N.C.) and food coloring (McCormick & Company, Inc., Md.) were used in the fabrication and characterization of the μPAD. A Micro-Pure deionizer was used to produce deionized (DI) water. Lake samples were collected from Maxey Park, Mackenzie Park, Hodges Park, and Buster Long Park in Lubbock, Tex. 10 mg/mL solutions of DI water and the colorimetric reagents (ninhydrin, litmus, and Ellman's reagent) were prepared. Stock solutions (10 test samples) of DI water and the metal ions ($NiSO_4$, $K_2Cr_2O_7$, and $HgCl_2$) were prepared at concentrations ranging from 0.03 to 20 ppm through 2-fold dilutions. A dimethylglyoxime-50% ethanol solution was prepared at a concentration of 10 mg/mL. A 1,5-diphenylcarbazide-50% acetone solution was prepared at a concentration of 10 mg/mL. A Michler's thioketone-50% acetone solution was prepared at a concentration of 10 mg/mL. An EDTA-DI water solution was prepared at a concentration of 0.05 mol/L. All solutions were stored in the dark until they were used.

Fabrication of the C-μPAD:

The C-μPADs were fabricated by depositing vaporized TCS on a masked chromatographic paper under a vacuum chamber. The details of this fabrication technique are demonstrated in the priority documentation, incorporated herein by reference. In brief, a fluidic pattern was drawn in AutoCAD and cut into a piece of polyvinyl tape (3M Inc.) with a vinyl cutter (Roland RX-1). The pattern was then affixed to a piece of chromatography paper, and this patterned paper was transferred to a vacuum chamber containing 100 μL of TCS on a heating block at 55° C. After 2 minutes of vapor deposition in the vacuum chamber, the patterned paper was removed from the vacuum chamber and placed on a 70° C. hot plate to remove the vinyl tape from the top of the paper. In this study, five different C-μPADs were fabricated using a chromatography paper: (1) a well-spot array 4 mm in diameter, (2) "Ni" and "Cr" fluidic patterns for the colorimetric analysis, (3) an eleven-zone well-spot array for the detection limit study, (4) a 3×3 well-spot array matrix for the specificity study, and (5) a floral pattern for the multiplex heavy metal ion detection. The floral-patterned C-μPAD featured a sample inlet and channels leading to four detection reservoirs. These channels allowed the liquid to reach the detection zones simultaneously.

Immobilization of Functional Groups on the C-μPADs:

First, the C-μPAD with the 4 mm well-spot array was fabricated on a piece of chromatography paper to immobilize three different functional groups. 2 μL solutions of DI water and APTES (amines), TESPSA (carboxyls), and MPTMS (thiols) with concentrations ranging from 0% to 5% were prepared and applied to each well-spot on the C-μPAD at 110° C. for 30 mm. During this functionalization procedure, the silane compounds were covalently bonded to the cellulose matrix on the chromatography paper. Unbound molecules were washed away with DI water, and the C-μPADs were gently dried at 50° C. Next, 10 mg/mL solutions of ninhydrin, litmus, and Ellman's reagent (which react with $NH_2$, COOH, and SH, respectively) were prepared and applied to each well in the functionalized C-μPAD to evaluate the immobilization capacities and distributions of these three functional groups. From these reactions, bluish-purple, orange, and yellow colors were developed on the well-spots, revealing the immobilization and concentration of each functional group. The RGB color differences were analyzed using ImageJ software, and ΔE (which represents the distance between red, green, and blue colors) was calculated using Euclidean distance:

$$\Delta E = \sqrt{(R_2-R_1)^2+(G_2-G_1)^2+(B_2-B_1)^2}.$$

Coupling of Colorimetric Reagents on the Functionalized Surface:

After immobilization, three colorimetric reagents were coupled to the functional groups. 2 μL of dimethylglyoxime was applied to the $NH_2$-functionalized surface, and the C-μPAD was then kept at 95° C. for 30 minutes to achieve coupling between the $NH_2$ and the —OH groups. In addition, 1,5-diphenylcarbazide was coupled to the COOH-functionalized surface. To achieve immobilization, 1-Ethyl-3-(3-dimethylaminopropyl)-carbodiimide (EDC) and N-hydroxysulfoxuccinimide (NHS) were applied to the COOH-functionalized surface to activate the COOH group. 2 μL of 1,5 diphenylcarbazide was then applied to the surface, and the C-μPAD was incubated at room temperature for 30 min. Michler's thioketone was immobilized for Hg (II) detection. First, 2 μL of EDTA was covalently bonded to the SH-functionalized surface. 2 μL of Michler's thioketone was then applied to the surface, and the C-μPAD was stored in the desiccator to minimize the oxidation of the chromogenic reagents until it was used in heavy metal detection.

Heavy Metal Detection with the C-μPAD:

After all of the chromogenic reagents were immobilized, colorimetric heavy metal detection was performed using the C-μPADs featuring the chemical symbols "Ni" and "Cr." To test their colorimetric responses, 50 μL solutions of Ni (II) metal ions and Cr (VI) metal ions were applied to the "Ni" and the "Cr" symbols patterned onto the C-μPADs, respectively. Additionally, heavy metal ion solutions with different concentrations were analyzed using the well-spot C-μPADs to determine the detection limit of each heavy metal ion. For each heavy metal ion, ten solutions with known concentrations between 0.03 ppm and 20 ppm were prepared and spotted onto three individual well-spot C-μPADs. 10 μL of metal ion solution and DI water (as a negative control) were applied to each of the well-spot C-μPADs. When the reactions were complete, the color development on each well-spot was observed. These colorimetric responses were imaged and quantitatively analyzed using ImageJ software to estimate the detection limit. To render the data consistently, all images were obtained 5 minutes after the reaction.

Specificity and Interference Analysis:

Three 3×3-well-spot C-μPADs were used for the specificity analysis. Each of the C-μPADs was modified by immobilizing the functional group and chromogenic reagents. APTES was immobilized in the first column of each device, TESPSA was immobilized in the second column of each device, and MPTMS was immobilized in the third column of each device. The colorimetric reagents were then coupled to the appropriate well spots. After surface modification, Ni (II), Cr (VI), and Hg (II) metal ion solutions were each applied to one device. Once the colorimetric reactions had occurred, the color intensities were measured in the manner described above. Interferences in heavy metal detection were analyzed using well-spot C-μPADs. A 200 ppm solution of NaCl and DI water and a 100 ppm solution of KCl and DI water were prepared. These solutions were each applied to a C-μPAD, and the interferences on the detection zone were monitored.

Figure 7:
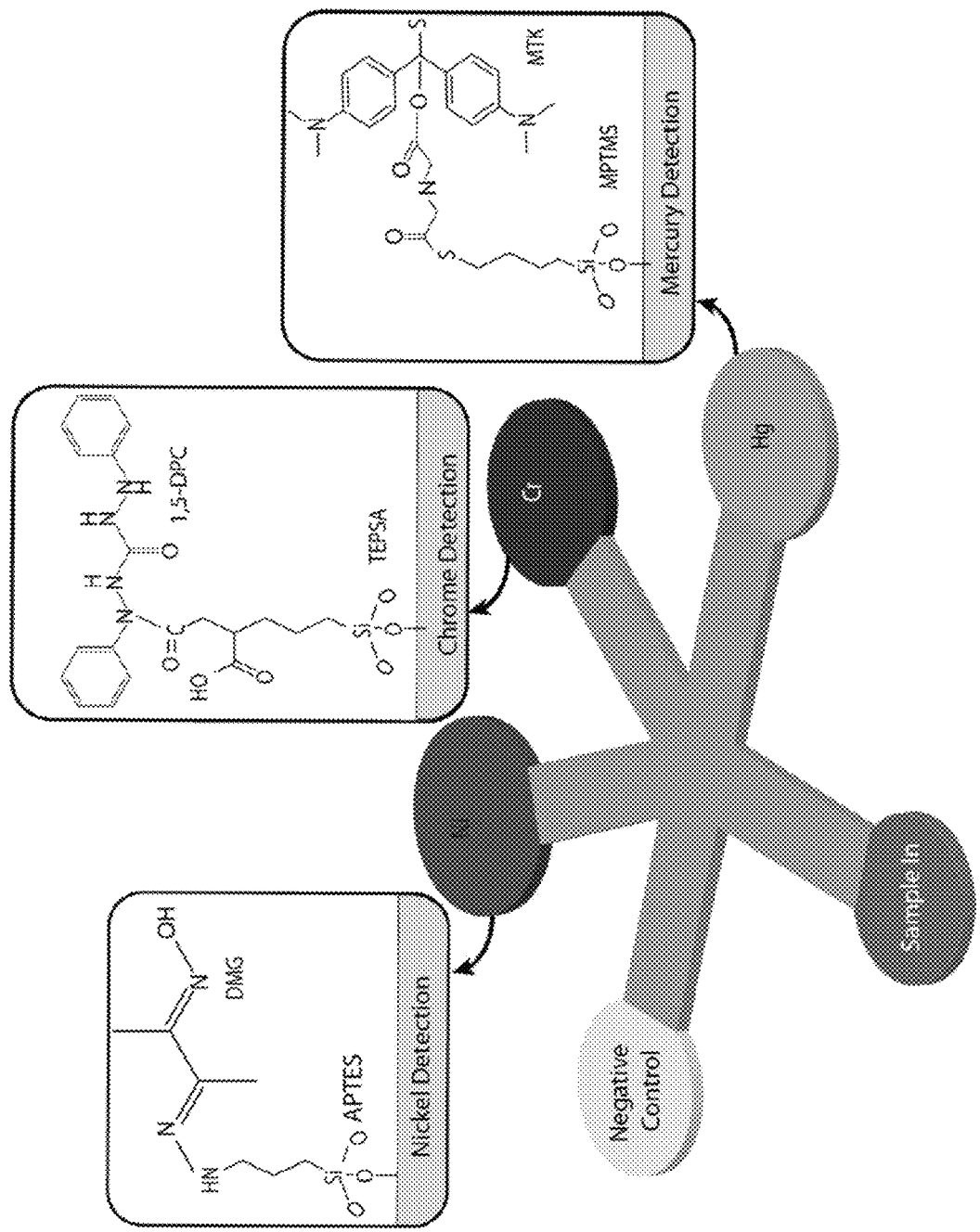
FIG. 7 depicts a schematic of the heavy metal detection pattern on the surface-modified multiplex C-µPAD, Amine, carboxyl, and thiol functional groups were immobilized on the detection zones of the multiplex C-µPAD and covalently coupled with colorimetric reagents in heavy metal detection.

Multiplex Heavy Metal Detection:

Multiplex heavy metal detection was demonstrated by identifying the heavy metal ions in lake water. At first, a floral-patterned multiplex C-µPAD with one inlet, a negative control and three detection zones were fabricated for multiplex heavy metal detection. Three detection zones on the multiplex C-µPAD were functionalized and coupled with colorimetric reagents as shown in FIG. 7. For real sample demonstrations, 4 lake-water samples were collected from four locations in Lubbock, Ill.: Maxey Park, Hodges Park, Mackenzie Park, and Buster Long Park. After measuring all lake-water samples, these lake-water samples were then spiked with standard metal ion solutions to achieve final concentrations of 5 ppm for Ni (II) and Cr (VI) and 0.3 ppm for Hg (II). Standard solutions with similar concentrations were prepared for comparison to estimate any cross-reactions. FIG. 11A summarizes four sets of mixture samples for demonstration of multiplexing capability. Each set of the mixture was applied to the inlet of the multiplex C-µPAD, from which point it traveled via a hydrophilic channel into the detection zone, where it formed a metal ion complex. The color development in the detection zone was analyzed and compared with the detection zone those obtained from the standard solutions. For determining the distribution of grayscale, respective images were converted to 8-bit gray scale using Image J. These histograms of each detection zone were obtained to determine the distribution of grayscale for each image.

Results and Discussion:

Immobilization of Colorimetric Reagents:

In this study, functional-group-terminated silane compounds and colorimetric reagents were pre-immobilized in the appropriate detection zones on a patterned chromatographic paper using simple condensation chemistry prior to heavy metal detection as shown in FIG. 7. The condensation process was used to covalently bind three functional-group-terminated silane compounds to the —OH groups of the cellulose fibers, producing Si—O—Si bridge of silane solutions and Si—O—C bonds between the cellulose fiber and silane solutions. The condensation process was carried out at 110° C. to successfully immobilize the functional groups onto the C-µPADs. Previously developed µPAD fabrication techniques such as wax printing and screen printing, are thermally unstable above 100° C. since the patterning materials intercalated with the fiber structures of a chromatographic paper are relatively low melting temperatures. In contrary, for C-µPAD technique, vaporized TCS molecules covalently bonded to the —OH groups of the fibers selectively using masking patterns so that well-defined hydrophobic barriers and hydrophilic channels were created on the paper with excellent thermal stability above 115° C. This chemical and thermal properties enable us to process thermal condensation reaction without breaking hydrophobic barriers.

Figure 8A:
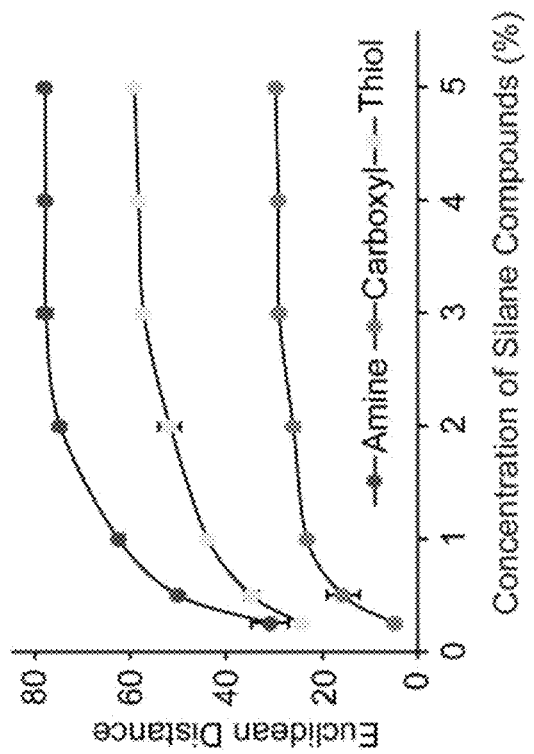
FIG. 8A-B depicts amine, carboxyl, and thiol functionalization on the well-spot array.
Figure 8B:
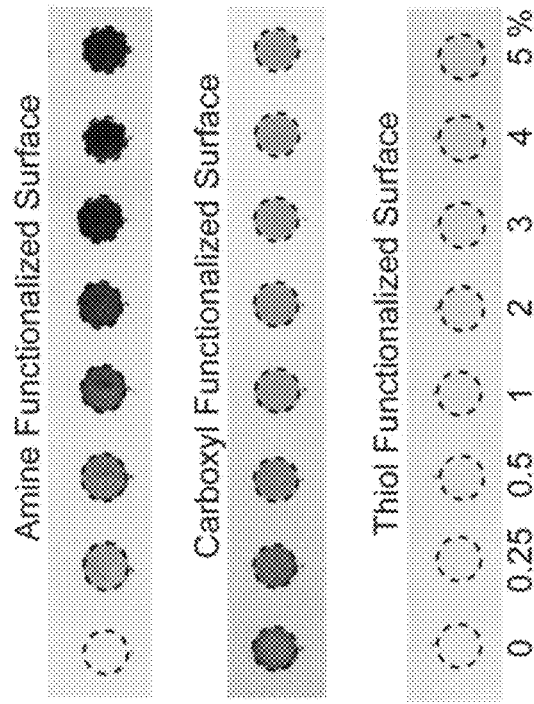
Figure 13:
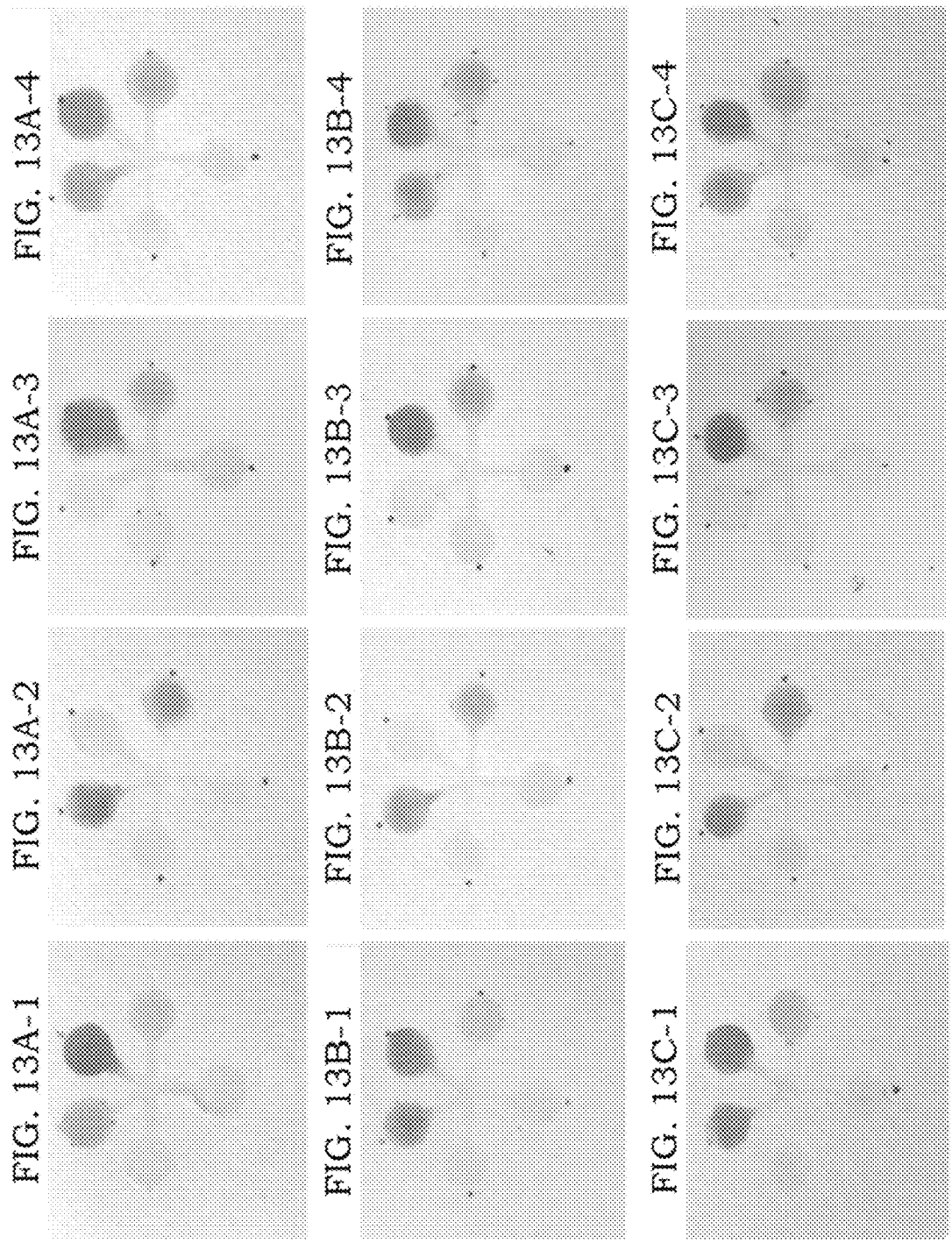
FIG. 13A(1)-C(4) depicts heavy metal detection on the multiplex C-µPAD pattern for spiked into three different lake samples. Each heavy metal ion was spiked into lake samples for the multiplex heavy metal detection and color was developed in the respective detection zone. There are almost no evidence of interferences and cross-contamination on the detection zone. (See FIG. 13A(1)-A(4).
FIG. 13B(1)-B(4), and FIG. 13C(1)-C(4)).

To find the optimum concentrations of the silane compounds, APTES, TESPSA, and MPTMS solutions with different concentrations were applied to the well spot of a C-µPAD. As is shown in FIG. 8A, the ninhydrin test, the litmus test, and the Ellman's test were used to confirm the functionalization of the $NH_2$, COOH, and SH, respectively. Ninhydrin reagents oxidized and reduced with the $NH_2$ group, producing a purple color that varied with the $NH_2$ concentration on the substrate. The color intensity increased as the $NH_2$ concentration increased, and no color change was obtained with 0% APTES. Litmus blue reagent reacted with the COOH group, changing the color from blue to orange to a degree that varied with the COOH concentration. The Ellman's reagents oxidized and reduced with the SH group, producing a yellow color whose intensity varied with the SH concentration. The colorimetric changes were imaged using ImageJ and analyzed using Euclidean distance. As FIG. 8B indicates, 3% functional-group-terminated silane compounds were sufficient to reach the saturation point with a uniform color distribution in each functionalized spot.

The detection zones of the C-µPADs were modified with functional groups to covalently immobilize the colorimetric reagents. The three colorimetric reagents were coupled with the $NH_2$-, COOH-, and SH-functionalized surface via the process shown in FIG. 7. Dimethylglyoxime is a colorimetric reagent for Ni (II) detection. Dimethylglyoxime was applied to an $NH_2$-functionalized surface, and hydrolysis was conducted at 95° C. to attach the dimethylglyoxime to the $NH_2$ functional group. 1,5-diphenylcarbazide is a calorimetric agent for Cr (VI) detection, and it was immobilized on the COOH functional group through carbodiimide coupling. In the detection of Hg (II), Michler's thioketone was immobilized on the SH group. To achieve this immobilization with high stability, EDTA was attached to the SH group as a masking agent via a dehydration process, and then Michler's thioketone was immobilized on it. To protect the Michler's thioketone from oxidation by air interferences from other metals should be minimized. Generally, the physical adsorption of molecules by µPADs often leads to reduced activity, poor uniformity, heterogeneity in colorimetric analysis, and disruption in quantitative analysis. However, covalent chemical bonding produces the most stable and uniform immobilizations onto C-µPADs. So, this functionalized C-µPAD would be a sensitive analytical device for heavy metal detection.

Heavy Metal Detection on the Functionalized C-µPAD:

After the colorimetric reagents were immobilized onto the functionalized surfaces, heavy metal detection was demonstrated on the chemical symbols "Ni" and "Cr," shown in FIG. 12. No leakage was observed from these patterns created using the C-µPAD method, even after multiple thermal condensation steps. Furthermore, this preliminary analysis revealed a homogenous color distribution without reducing any chromogenic reactivity. The performance of the functionalized C-µPAD was investigated by using various concentrations of heavy metals. 10 µL of different metal ion solutions—Ni (II), Cr (VI) and Hg (II)—was dropped into each well of a well-spot C-µPAD. The metal ions reacted with their respective colorimetric reagents, forming colored metal complexes on the well-spots within 1 minute. FIG. 9A-C shows the color intensities of the metal complexes formed by the ten concentrations of metal ions. It also shows a negative control in the center spot. Ni (II) reacted with dimethylglyoxime to create a complex with a deep pink color on the well-spot. Cr (VI) reacted with 1,5 diphenylcarbazide to create a complex with a purple color on the well-spot. Hg (II) solution created a Michler's thioketone-Hg (II) complex with a brown color. Color intensity decreased with metal concentration, and no color development was obtained in the negative-control zone. FIG. 9D-F shows the Euclidean distances for the metal ion concentrations. Importantly, colorimetric responses were obtained at and above 0.15 ppm for Ni (II) and Cr (VI) and at and above 0.075 ppm for Hg (II), and no significant colorimetric responses were obtained below these levels. This represents a twofold improvement over previous reports due to the homogeneous metal ion complexes' formation from immobilized chromogenic reagents. In addition, functional-group-terminated silane substrates can separate, pre-concentrate, and extract various metals from water samples, and the higher extraction capacity of the functionalized surface enriches the metal ions in the detection zone.[44, 45] In colorimetric analysis, maintaining the pHs of the colorimetric reagents improves reaction efficiency. Ammonium hydroxide was used to keep the pH of the dimethylglyoxime at 9 5.[4] The $NH_2$-functionalized surface did not require any additional reagents to maintain its pH, however, because the $NH_2$ group itself kept the pH above 9.5. Previously, quantitative analysis was the major challenge in the µPAD based heavy metal detection since the metal complexes easily flushed away or migrated towards the edges and heterogenous color formation on the detection zones. The chemically functionalized spot exhibited the homogenous color distribution throughout the detection zone that leads to the quantitative analysis.

Furthermore, since various metal ions and minerals are ubiquitous in real-world samples, it is important to assess the specificity of an analysis and identify interferences. To measure the specificity of the analysis, colorimetric reagents were applied to each column of three separate 3×3 well-spot C-µPADs. As shown in FIG. 10A-C, a pink dimethylglyoxime-Ni (II) complex was generated on the first column of the first device, and no color appeared on the other two columns. A purple 1,5 diphenylcarbazide-Cr (VI) complex formed on the second column of the second device, and no color appealed on the other two columns. A brown Michler's thioketone-Hg (II) complex was formed on the third column of the third device, and no color appeared on the other two columns. As shown in FIG. 10D, the Euclidean distances confirmed that the metal complexes formed in their designed zones and that there was no cross-reaction between the metals. Interferences were evaluated using high concentrations of NaCl and KCl, which are well-known chemical components in drinking water. As we expected, there were no significant interferences during any of the three reactions. In addition, we used metal-selective chromogenic reagents and EDTA to eliminate the interferences. Metal-selective chromogenic reagents dimethylglyoxime and 1,5 diphenylcarbazide eliminated the cross-reaction between the other metal ions. Michler's thioketone has the capacity to react with other metal ions and minerals. However, the masking reagent EDTA chelated the complex formation of the other metal ions, except for the Michler's thioketone-Hg (II) complex.

Figure 14:
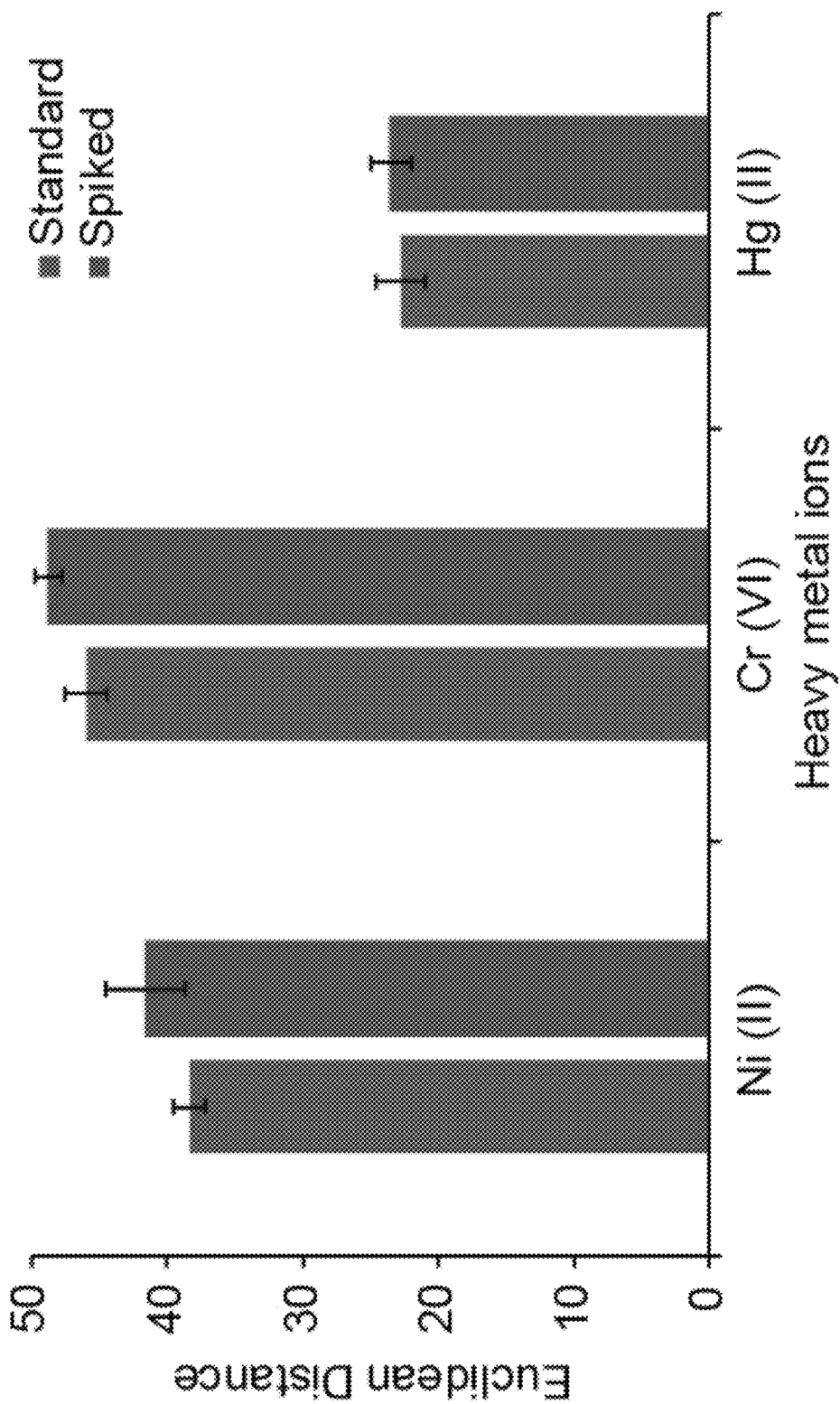
FIG. 14 depicts comparative analysis of heavy metal ions using multiplex C-µPAD shows the color intensities of the lake samples are almost corresponded to the standard samples.

Multiplex Heavy Metal Detection with Environmental Samples:

To demonstrate the applicability of the functionalized C-µPAD for detecting heavy metals using real environmental samples, lake-water samples were collected and tested. Inductively coupled plasma mass spectrometry (ICPMS) analysis of the lake water revealed that no metal ions were present at levels above 0.075 ppm and that all were present at levels below their respective detection limits. These lake-water samples were then spiked with high and low concentrations of Ni (II), Cr (VI) and Hg (II). Both the standard and the spiked lake-water samples were prepared with 5 ppm of Ni (II) and Cr (VI) and 0.3 ppm of Hg (II), which are normally present in environmental water from the environmental protection agency (EPA) reports.[46-48] Using four sets of mixture samples shown in FIG. 11A, each mixture sample was then applied to the sample inlet and reacted with their respective colorimetric reagents, producing the colors in their respective zones. FIG. 11B-E, FIG. 11F-I, and FIG. 13 (A-1 through C-4) show the multiplex heavy metal detection for the standard and spiked lake samples. Both the standard samples and the lake samples formed metal complexes in their designated detection zones without any cross-reactions. FIG. 14 shows the Euclidean distance for spiked lake sample and standard sample, which analyzed from FIGS. 11E and I. The color intensities obtained for the lake samples almost corresponded to those obtained for the standard samples. From this comparison, we confirmed that the variation in the pH values of the lake samples (from pH 5.5 to 7.5) did not affect significantly to overall reaction efficiency and sensitivity. Previously, heavy metal ions were recovered from tap water and lake water; the tap water was boiling for 5 min to remove the chlorine and the membrane filter was used to remove solids from lake water prior to the heavy metal detection using hydrogel aptasensor. However, these pre-processing step required extra effort to remove all possible containments and cross-reactive chemicals. Instead, without any pre-treatment processes, we evaluated any bias effect from any contaminants and cross-reactive chemicals. From untreated lake samples, we confirmed that other minerals and metal ions in the lake samples also did not reduce the reaction efficiency, the sensitivity, or the specificity of the functionalized C-µPAD.

Figure 15A:
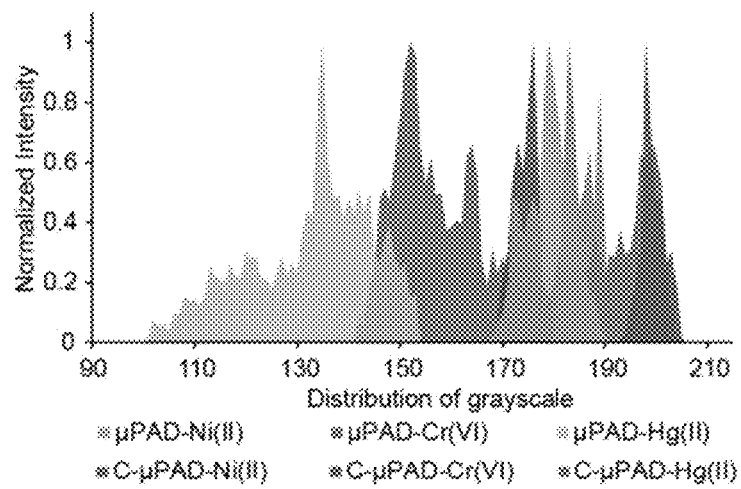
FIG. 15A-C depicts color histograms from various µPAD approaches to detect multiple target samples. (FIG. A-B) The distribution of pixels among 8-bit grayscale of three heavy metal detection using µPAD and C-µPAD.
Figure 15B:
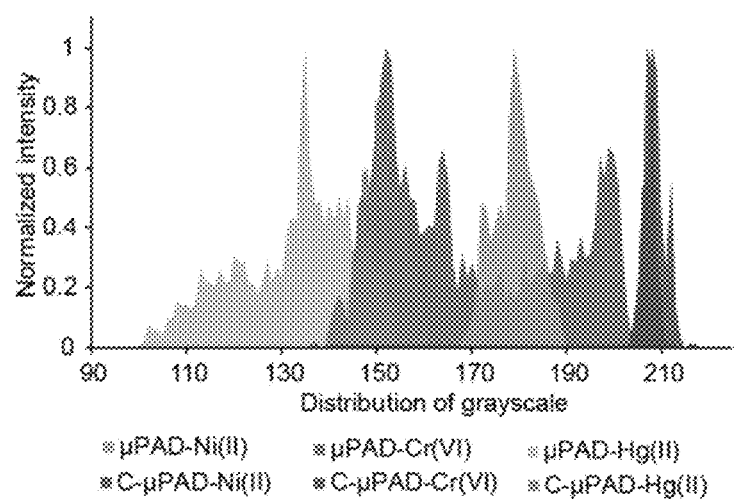
Figure 15C:
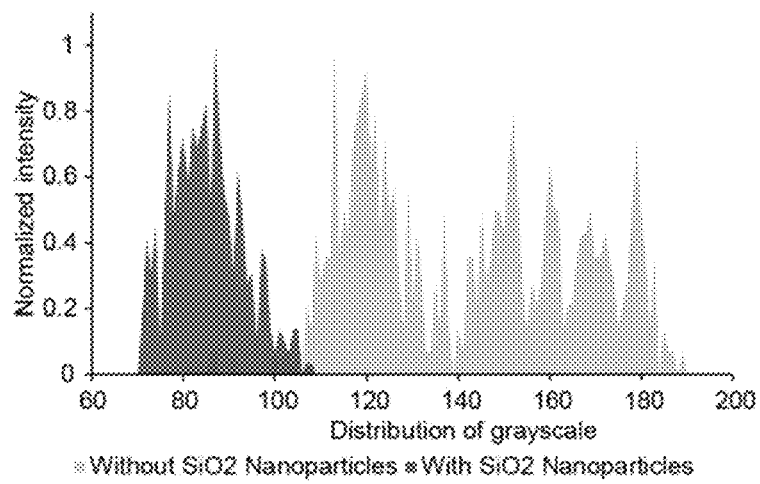

In addition, C-µPAD shows the excellent uniformity on detection zone. In general, poor color uniformity associated with colorimetric measurements on µPADs is one of the most important shortcomings on µPADs. By improving the uniformity, the sensitivity, reliability, and reproducibility of quantitative analysis using µPADs can be significantly enhanced.[30, 32, 50] FIG. 11J shows histogram graphs, showing color distribution of FIG. 11E. These histograms show that the ranges of color distribution are 12.67 for Ni (II), 14.33 for Cr (VI), and 13.00 for Hg (II) from the standard heavy metal samples. The histogram for Ni (II) shows the better uniformity than other two analytes. Table 1 and FIG. 15 present the distribution of pixels among 8-bit grayscale of three different approaches which are standard µPAD for heavy metal detection, $SiO_2$ nanoparticles-coupled µPAD for glucose detection, and C-µPAD for heavy metal detection.

TABLE 1

Color distribution ranges from three different approaches.

| Surface Treatment on µPAD | Targets | Distribution of grayscale |
|---|---|---|
| Surface modification with nanoparticles [32] | Without $SiO_2$ NP for glucose assay | 84.33 |
| | With $SiO_2$ NP for glucose assay | 40.67 |
| Standard µPAD [4] | 0.5 ppm of Ni (II) | 25.00 |
| | 0.5 ppm of Cr (VI) | 59.33 |
| | 0.5 ppm of Hg (II) | 54.00 |
| Chemically functionalized C-µPAD #1 (FIG. 11e) | 5 ppm of Ni (II) | 12.67 |
| | 5 ppm of Cr (VI) | 14.33 |
| | 0.3 ppm of Hg (II) | 13.00 |
| Chemically functionalized C-µPAD #2 (FIG. 9) | 0.6 ppm of Ni (II) | 9.67 |
| | 0.6 ppm of Cr (VI) | 14.33 |
| | 0.6 ppm of Hg (II) | 28.33 |

As shown in Table 1, the ranges of grayscale distribution are 84.33 for a standard µPAD and 40.67 for $SiO_2$ nanoparticles-coupled µPAD. The uniformity of grayscale distribution has improved for glucose assay up to 52% using $SiO_2$ nanoparticles-coupled µPAD. Furthermore, the ranges of grayscale distribution are 9.67 for Ni (II), 14.33 for Cr (VI) and 28.33 for Hg (II) on C-µPAD, while the color distribution of 0.5 ppm of heavy metal ions sample are 25.00 for Ni (II), 59.33 for Cr (VI) and 54.00 for Hg (II) on standard µPAD. With the chemically functionalized C-µPAD, the uniformity improved up to 76% than that of standard µPADs. By lowering down color distribution with surface modified µPADs, high reliability, precision, and sensitivity of this C-µPAD could achieve for quantitative colorimetric analysis The C-µPAD platform as disclosed in accordance with the exemplary embodiments set forth herein is repeatable, versatile, and cost effective. The chemical application allows for the creation of complex channels. A wide variety of channels can be created using the settling time calculated from the calibration results. The new method does not affect the properties of the paper in the hydrophilic channel area.

It is therefore an embodiment to successfully immobilize different functional groups and colorimetric reagents on C-µPADs to detect heavy metals in water samples. The colorimetric analysis exhibited a high detection sensitivity and detection limits as low as 0.15 ppm for Ni (II) and Cr (VI) and 0.075 ppm for Hg (II). The distribution of the homogenous metal complexes across the detection zones indicates that the surface-functionalized C-µPAD can be used to achieve precise quantitative determination and rapid, user-friendly, and low-cost detection. Since it can identify individual metal ions in a mixture of metal ions, exhibiting no interferences from foreign metal ions or minerals, it could be used to identify individual metal ions in mixtures of metal ions. Additionally, the portability of the C-µPAD for multiplex heavy metal detection could be increased by integrating a simple RGB sensor to quantify the color intensity. This RGB sensor could be wirelessly connected to a smartphone, enabling user-friendly data collection. This platform can be easily extended for detecting other environmental monitoring targets and for point-of-care diagnostics.

Further, the CVD method to form hydrophilic-hydrophobic barriers by depositing vaporized TCS on a chromatography paper. TCS treated region on the paper established strong hydrophobic layers compared to an untreated chromatography paper. This C-µPAD technique is a simple, rapid, and thermally insensitive procedure compared to the previously reported µPAD fabrication techniques. In addition, this C-µPAD technique has a high commercial potential with low-cost fabrication and mass production capabilities. With this C-µPAD technique, various bioassays such as glucose and immunoassay have been demonstrated with clinically relevant LODs. Furthermore, all assays were performed with ~5 µL target sample volume without the use of a spectrophotometer or other advanced equipment. All assay demonstrations show that this C-µPAD enables us to revolutionize POC diagnostics by further validations with clinical samples. Additional assay demonstrations such as cardiac panel, cytokines, and liver panel screenings are required to show adaptability of this platform. The heavy metal detection analysis proves that the C-µPAD is capable to detect the environmental contaminants by immobilizing amine functional group using thermal condensation. Functionalizing the C-µPAD using thermal condensation is a significant achievement to improve stability, sensitivity, and specificity for point-of-care chemical and biological analysis. With extension, other functional groups such as carboxyl and thiol terminated silane compounds can be easily immobilized for conjugating nucleic acids, proteins, hormones, drugs, and enzymes selectively for multiplexing biological and chemical analysis Those skilled in the art will recognize that the devices, methods, and systems of the present invention may be implemented in many manners and as such are not to be limited by the foregoing exemplary embodiments and examples. Furthermore, the embodiments of methods presented and described in this disclosure are provided by way of example in order to provide a more complete understanding of the technology. The disclosed methods are not limited to the operations and logical flow presented herein. Alternative embodiments are contemplated in which the order of the various operations is altered and in which suboperations described as being part of a larger operation are performed independently.

REFERENCES

[1] M. Li, R. Cao, A. Nilghaz, L. Guan, X. Zhang, W. Shen, "Periodic-Table-Style" paper device for monitoring heavy metals in water, Anal. Chem. 87 (2015) 2555-2559.

[2] R. S. Boyd, Heavy metal pollutants and chemical ecology: exploring new frontiers, J. Chem. Ecol. 36 (2010) 46-58.

[3] N. Johri, G. Jacquillet, R. Unwin, Heavy metal poisoning: the effects of cadmium on the kidney, Biometals 23 (2010) 783-792.

[4] S. M. Z. Hossain, J. D. Brennan, β-Galactosidase-based colorimetric paper sensor for determination of heavy metals, Anal. Chem. 83 (2011) 8772-8778.

[5] V. A. Lemos, A. L. de Carvalho, Determination of cadmium and lead in human biological samples by spectrometric techniques: a review, Env. Monitor. Assess. 171 (2010) 255-265.

[6] D. J. Butcher, Advances In Inductively Coupled Plasma Optical Emission Spectrometry For Environmental Analysis, Instrum. Sci. Technol. 38 (2010) 458-469.

[7] J. Feldmann, P. Salaün, E. Lombi, Critical review perspective: elemental speciation analysis methods in environmental chemistry moving towards methodological integration, Environ. Chem. 6 (2009) 275-289.

[8] M. Li, H. Gou, I. Al-Ogaidi, N. Wu, Nanostructured sensors for detection of heavy metals: a review, ACS Sustainable Chem. Eng. 1 (2013) 713-723.

[9] Y. Lin, D. Gritsenko, S. Feng, Y. C. Teh, X. Lu, J. Xu, Detection of heavy metal by paper-based microfluidics, Biosens. Bioelectron. 83 (2016) 256-266.

[10] Y. Tian, Y. Wang, Y. Xu, Y. Liu, D. Li, C. Fan, A highly sensitive chemiluminescence sensor for detecting mercury (II) ions: a combination of Exonuclease III-aided signal amplification and graphene oxide-assisted background reduction, Sci. China Chem. 58 (2015) 514-518.

[11] N. S. Kou, W. Shumi, M. H. Lee, S. W. Bae, J. Du, J. S. Kim, J. I. Hong, X. Peng, J. Yoon, S. Park, Microfluidic detection of multiple heavy metal ions using fluorescent chemosensors, Bull. Korean Chem. Soc. 30 (2009) 1173-1176.

[12] T. Krawczyński vel Krawczyk, M. Moszczyńska, M. Trojanowicz, Inhibitive determination of mercury and other metal ions by potentiometric area biosensor, Biosens. Bioelectron. 15 (2000) 681-691.

[13] X. Li, J. Tian, T. Nguyen, W. Shen, Paper-based microfluidic devices by plasma treatment, Anal. Chem. 80 (2008) 9131-9134.

[14] K. Abe, K. Suzuki, D. Citterio, Inkjet-printed microfluidic multianalyte chemical sensing paper, Anal. Chem. 80 (2008) 6928-6934.

[15] A. W. Martinez, S. T. Phillips, M. J. Butte, G. M. Whitesides, Patterned paper as a platform for inexpensive, low-volume, portable bioassays, Angew. Chem. Int. Ed. Engl. 46 (2007) 1318-1320.

[16] D. A. Bruzewicz, M. Reches, G. M. Whitesides, Low-cost printing of poly(dimethylsiloxane) barriers to define microchannels in paper, Anal. Chem. 80 (2008) 3387-3392.

[17] S. Su, M. M. Ali, C. D. M. Filipe, Y. Li, R. Pelton, Microgel-based inks for paper-supported biosensing applications, Biomacromolecules 9 (2008) 935-941.

[18] A. W. Martinez, S. T. Phillips, G. M. Whitesides, Three-dimensional microfluidic devices fabricated in layered paper and tape, Proc. Natl. Acad. Sci. U.S.A. 105 (2008) 19606-19611.

[19] J. Liu, H. Wang, N. E. Manicke, J. M. Lin, R. G. Cooks, Z. Ouyang, Development, characterization, and application of paper spray ionization, Anal. Chem. 82 (2010) 2463-2471.

[20] A. Apilux, W. Dungchai, W. Siangproh, N. Praphairaksit, C. S. Henry, O. Chailapakul, Lab-on-Paper with dual electrochemical/colorimetric detection for simultaneous determination of gold and iron, Anal. Chem. 82 (2010) 1727-1732.

[21] H. Noh, S. T. Phillips, Metering the Capillary-driven flow of fluids in paper-based microfluidic devices, Anal. Chem. 82 (2010) 4181-4187.

[22] M. S. Khan, G. Thouas, W. Shen, G. Whyte, G. Garnier, Paper diagnostic for instantaneous blood typing, Anal. Chem. 82 (2010) 4158-4164.

[23] A. W. Martinez, S. T. Phillips, E. Carrilho, S. W. Thomas, H. Sindi, G. M. Whitesides, Simple telemedicine for developing regions: camera phones and paper-based microfluidic devices for real-time, off-site diagnosis, Anal. Chem. 80 (2008) 3699-3707.

[24] R. Pelton, Bioactive paper provides a low-cost platform for diagnostics, Trends Anal. Chem. 28 (2009) 925-942.

[25] X. Li, J. Tian, W. Shen, Thread as a versatile material for low-cost microfluidic diagnostics, Appl. Mater. Interfaces 2 (2010) 1-6.

[26] Y. Lu, W. Shi, J. Qin, B. Lin, Fabrication and characterization of paper-based microfluidics prepared in nitrocellulose membrane by wax printing, Anal. Chem. 82 (2010) 329-335.

[27] W. Zhao, M. M. Ali, S. D. Aguirre, M. A. Brook, Y. Li, Paper-based bioassays using gold nanoparticle colorimetric probes, Anal. Chem. 80 (2008) 8431-8437.

[28] A. W. Martinez, S. T. Phillips, G. M. Whitesides, E. Carrilho, Diagnostics for the developing world: microfluidic paper-based analytical devices, Anal. Chem. 82 (2010) 3-10.

[29] R. E. Luckham, J. D. Brennan, Bioactive paper dipstick sensors for acetylcholinesterase inhibitors based on sol-gel/enzyme/gold nanoparticle composites, Analyst 135 (2010) 2028-2035.

[30] E. Evans, E. F. M. Gabriel, W. K. T. Coltro, C. D. Garcia, Rational selection of substrates to improve color intensity and uniformity on microfluidic paper-based analytical devices, Analyst 139 (2014) 2127-2132.

[31] D. L. Giokas, G. Z. Tsogas, A. G. Vlessidis, Programming fluid transport in paper-based microfluidic devices using razor-crafted open channels, Anal. Chem. 86 (2014) 6202-6207.

[32] E. Evans, E. F. M. Gabriel, T. E. Benavidez, W. K. T. Coltro, C. D. Garcia, Modification of microfluidic paper-based devices with silica nanoparticles, Analyst 139 (2014) 5560-5567.

[33] P. de Tarso Garcia, T. M. Garcia Cardoso, C. D. Garcia, E. Carrilho, W. K. Tomazelli Coltro, A handheld stamping process to fabricate microfluidic paper-based analytical devices with chemically modified surface for clinical assays, RSC Adv. 4 (2014) 37637-37644.

[34] M. M. Mentele, I. Cunningham, K. Koehler, J. Volckens, C. S. Henry, Microfluidic paper-based analytical device for particulate metals, Anal. Chem. 84 (2012) 4474-4480.

[35] T. Lam, J. P. Devadhasan, R. Howse, J. Kim, A Chemically patterned microfluidic paper-based analytical device (C-µPAD) for point-of-care diagnostics, Sci. Rep. 7 (2017) 1188.

[36] S. Gaurav, Digital color imaging handbook, CRC Press, 1.7.2 ed (2003).

[37] A. Valberg, Light vision color, Wiley, ISBN 9780470849026 (2005).

[38] R. K. Werner Backhaus, John Simon Werner, Color vision: Perspectives from different disciplines, Walter de Gruyter, ISBN 9783110154313 (1998).

[39] D. Deza Elena, Michel marie encyclopedia of distances, Springer, (2009).

[40] M. A. Andreas Koschan, Digital color image processing, ISBN: 978-0-470-14708-5 (2008).

[41] M. Abdelmouleh, S. Boufi, M. N. Belgacem, A. Dufresne, Short natural-fibre reinforced polyethylene and natural rubber composites: Effect of silane coupling agents and fibres loading, Compos. Sci. Technol. 67 (2007) 1627-1639.

[42] H. Koga, T. Kitaoka, A. Isogai, In situ modification of cellulose paper with amino groups for catalytic applications, J. Mater. Chem. 21 (2011) 9356-9361.

[43] M. E. Vlachopoulou, A. Tserepi, P. Pavli, P. Argitis, M. Sanopoulou, K. Misiakos, A low temperature surface modification assisted method for bonding plastic substrates, J. Micromech. Microeng. 19 (2009) 015007.

[44] P. K. Jal, S. Patel, B. K. Mishra, Chemical modification of silica surface by immobilization of functional groups for extractive concentration of metal ions, Talanta 62 (2004) 1005-1028.

[45] H. Lee, J. Yi, Removal of copper ions using functionalized mesoporous silica in aqueous solution, Sep. Sci. Technol. 36 (2001) 2433-2448.

[46] P. B. Tchounwou, C. G. Yedjou, A. K. Patlolla, D. J. Sutton, Heavy metals toxicity and the environment, EXS 101 (2012) 133-164.

[47] D. Oakley, N. E. Korte, Nickel and chromium in ground water samples as influenced by well construction and sampling methods, Ground Water Monit. Remediat. 16 (1996) 93-99.

[48] D. A. Wentz, M. E. Brigham, L. C. Chasar, M. A. Lutz, D. P. Krabbenhoft, Mercury in the Nation's streams—Levels, trends, and implications: USGS 1395 (2014) 1-90.

[49] B. F. Ye, Y. J. Zhao, Y. Cheng, T. T. Li, Z. Y. Xie, X. W. Zhao, et al., Colorimetric photonic hydrogel aptasensor for the screening of heavy metal ions, Nanoscale 4 (2012) 5998-6003.

[50] E. L. Rossini, M. I. Milani, E. Carrilho, L. Pezza, H. R. Pezza, Simultaneous determination of renal function biomarkers in urine using a validated paper-based microfluidic analytical device, Anal Chim. Acta 997 (2018) 16-23.

What is claimed is:
1. A method comprising:
(a) selecting a microfluidic paper-based analytical device (µPAD), wherein the µPAD comprises:
(i) one or more hydrophobic barriers of a hydrophobic material deposed on a substrate layer, wherein the one or more hydrophobic barriers define one or more fluidic channels,
(ii) one or more detection compounds attached via covalent bonding to the substrate layer in the one or more fluidic channels, wherein the one or more detection compounds each have at least one functional group, wherein an attachment via covalent bonding of the detection compounds to the substrate layer is based on one or more analytes of interest, and (iii) one or more chromogenic reagents immobilized onto the one or more detection compounds;

(b) channeling a fluid through at least one of the one or more fluid channels, wherein the fluid comes in contact with the one or more chromogenic reagents; and (c) detecting the one or more analytes of interest in the fluid based upon a reaction between the one or more analytes of interest and the one or more chromogenic reagents, wherein the detection comprises the one or more chromogenic reagents changing visual color when the one or more analytes of interest react with the one or more chromogenic reagents.

2. The method of claim 1, wherein the one or more detection compounds are selected from a group consisting of: (3-aminopropyl) tri-ethoxysilane (APTES), triethoxysiloslylpropyl succinic anhydride (TESPSA), (3-Mercaptopropyl) trimethoxysilane (MPTMS), human TNFα biotinylated antibody, straptabividin-HRP reagent, 1-Ethyl-3-(3-dimethylaminopropyl)-carbodiimide (EDC), N-hydroxysuccinimide (NHS), N-hydroxysulfoxuccinimide (sulfo-NHS), and combinations thereof.

3. The method of claim 1, wherein the one or more detection compounds comprise an assay reagent.

4. The method of claim 1, wherein the one or more detection compounds comprise an assay reagent that is an enzyme selected from a group consisting of: o-dianisidine, glucose peroxidase, glucose oxidase, horseradish peroxidase, uricase, amine terminated magnetic particles, carbodiimide coupled enzymes, and combinations thereof.

5. The method of claim 4, further comprising utilizing one or more amine-functionalized silica microparticles which immobilize one or more enzymes.

6. The method of claim 1, wherein the one or more chromogenic reagents are colorimetric, chemiluminescent, luminescent, or combinations thereof.

7. The method of claim 1, wherein the one or more chromogenic reagents are selected from a group consisting of: horseradish peroxidase (HRP), dimethylglioxome (DMG), 1,5 diphenylcarbazide, Michler's thioketone, and combinations thereof.

8. The method of claim 1, wherein the one or more analytes of interest are selected from the group consisting of: glucose, TNFα, respiratory disease markers, HIV, HBV, and metal ions.

9. The method of claim 1, wherein the one or more analytes of interest are one or more heavy metals.

10. A method for preparing a chemically patterned microfluidic paper-based analytical device (C-µPAD), comprising:

(a) forming one or more hydrophobic barriers by chemical vapor deposition (CVD) of a hydrophobic material on a substrate layer defining one or more fluidic channels, wherein the substrate layer is a layer of a substrate;

(b) attaching a detection compound having at least one functional group via covalent bonding to the substrate in the one or more fluidic channels on the substrate layer, an attachment via covalent bonding of the detection compound to the substrate being based on one or more analytes of interest; and (c) immobilizing onto the functional group one or more chromogenic reagents, wherein
(i) the one or more hydrophobic barriers define one or more fluidic channels through which a fluid can be channeled so that the fluid comes in contact with the one or more chromogenic reagents,
(ii) the one or more chromogenic reagents are operable to react with the one or more analytes of interest that are in the fluid, and
(iii) the one or more chromogenic reagents are operable to change visual color when the one or more analytes of interest react with the one or more chromogenic reagents.

11. The method of claim 10 wherein the detection compound is selected from a group consisting of: (3-aminopropyl) tri-ethoxysilane (APTES), triethoxysiloslylpropyl succinic anhydride (TESPSA), (3-Mercaptopropyl) trimethoxysilane (MPTMS), human TNFα biotinylated antibody, straptabividin-HRP reagent, 1-Ethyl-3-(3-dimethylaminopropyl)-carbodiimide (EDC), N-hydroxysuccinimide (NHS), N-hydroxysulfoxuccinimide (sulfo-NHS), and combinations thereof.

12. The method of claim 10, wherein the detection compound comprises an assay reagent.

13. The method of claim 10, wherein the detection compound comprises an assay reagent that is an enzyme selected from a group consisting of: o-dianisidine, glucose peroxidase, glucose oxidase, horseradish peroxidase, uricase, amine terminated magnetic particles, carbodiimide coupled enzymes, and combinations thereof.

14. The method of claim 13, further comprising utilizing one or more amine-functionalized silica microparticles which immobilize one or more enzymes.

15. The method of claim 10, wherein the one or more chromogenic reagents are colorimetric, chemiluminescent, luminescent, or combinations thereof.

16. The method of claim 10, wherein the one or more chromogenic reagents are selected from a group consisting of: horseradish peroxidase (HRP), dimethylglioxome (DMG), 1,5 diphenylcarbazide, Michler's thioketone, and combinations thereof.

17. The method of claim 10, wherein the one or more analytes of interest are selected from the group consisting of: glucose, TNFα, respiratory disease markers, HIV, HBV, and metal ions.

18. The method of claim 10, wherein the one or more analytes of interest are one or more heavy metals.

* * * * *